(12) United States Patent
Nakaoka et al.

(10) Patent No.: US 7,774,048 B2
(45) Date of Patent: Aug. 10, 2010

(54) FLUORESCENT ENDOSCOPE DEVICE

(75) Inventors: Masaya Nakaoka, Hachioji (JP); Akira Hasegawa, Musashino (JP)

(73) Assignee: Olympus Corporation, Tokyo (JP)

( * ) Notice: Subject to any disclaimer, the term of this patent is extended or adjusted under 35 U.S.C. 154(b) by 1164 days.

(21) Appl. No.: 11/294,572

(22) Filed: Dec. 6, 2005

(65) Prior Publication Data

US 2007/0016077 A1  Jan. 18, 2007

(30) Foreign Application Priority Data

Dec. 8, 2004 (JP) .............................. 2004-355661
Dec. 1, 2005 (JP) .............................. 2005-347849

(51) Int. Cl.
*A61B 6/00* (2006.01)
(52) U.S. Cl. ...................... 600/478; 600/473; 600/476; 600/466
(58) Field of Classification Search .................. None
See application file for complete search history.

(56) References Cited

U.S. PATENT DOCUMENTS

| | | | |
|---|---|---|---|
| 5,111,821 A | * | 5/1992 | Potter .......................... 600/431 |
| 5,749,830 A | * | 5/1998 | Kaneko et al. .............. 600/160 |
| 5,769,792 A | | 6/1998 | Palcic et al. |
| 6,070,096 A | * | 5/2000 | Hayashi ....................... 600/477 |
| 6,422,994 B1 | | 7/2002 | Kaneko et al. |
| 6,678,398 B2 | | 1/2004 | Wolters et al. |
| 2004/0158300 A1 | * | 8/2004 | Gardiner ...................... 607/88 |

FOREIGN PATENT DOCUMENTS

| | | |
|---|---|---|
| EP | 1 553 408 A1 | 7/2005 |
| WO | WO 03/079015 A1 | 9/2003 |

\* cited by examiner

*Primary Examiner*—Long V Le
*Assistant Examiner*—Joel F Brutus
(74) *Attorney, Agent, or Firm*—Arnold International; Bruce Y. Arnold

(57) ABSTRACT

An endoscope device includes a light source unit that creates multiple excitation lights having different peak wavelengths, an illumination unit, and an imaging unit that includes an objective optical system and an image pickup device. The imaging unit is capable of acquiring images of fluorescent lights having different peak wavelengths that are emitted by multiple fluorescent substances contained in a living organism. The illumination unit transmits the excitation lights to a tip of the endoscope device, and the multiple excitation lights are then directed so as to illuminate a living organism that contains multiple fluorescent substances. A variable transmittance optical element or an array of different type of filters may be placed before the image pickup device to separately detect the multiple fluorescent substances. Specified conditions and transmittances for the variable transmittance optical element and filters are disclosed to insure that the multiple fluorescent substances may be separately detected.

35 Claims, 25 Drawing Sheets

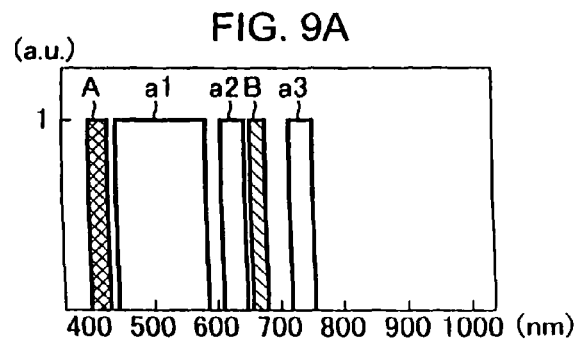
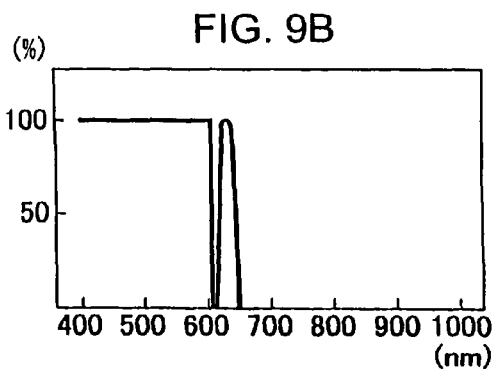
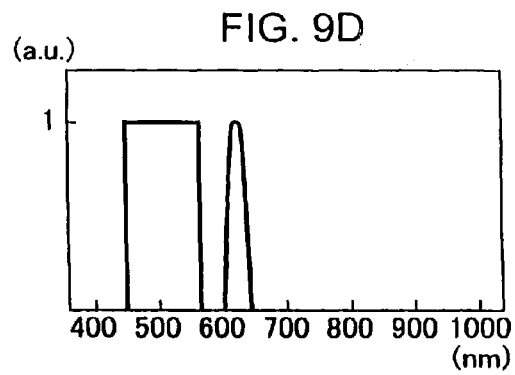
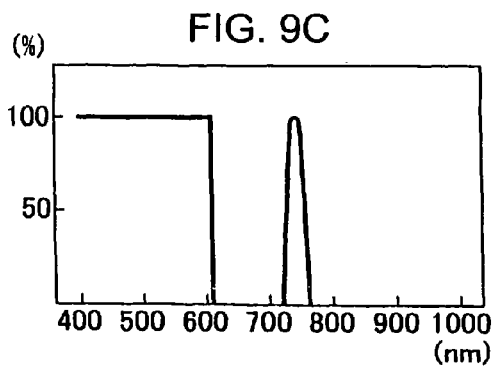
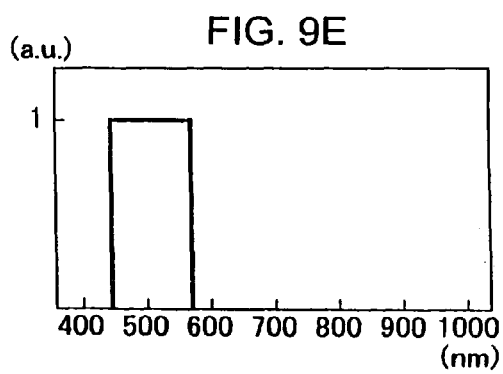
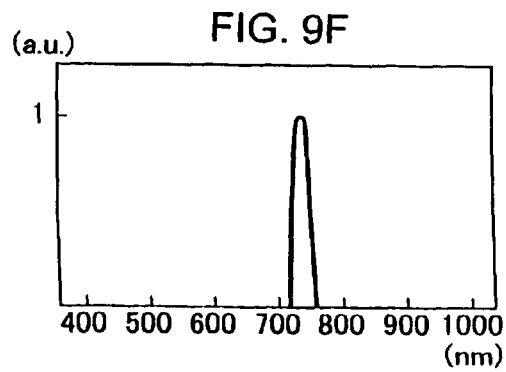

FLUORESCENT ENDOSCOPE DEVICE

CROSS-REFERENCE TO RELATED APPLICATIONS

This application claims the benefit of priority of JP 2004-355661 filed Dec. 8, 2004 and of JP 2005-347789 filed Dec. 1, 2005, both of which are hereby incorporated by reference.

BACKGROUND OF THE INVENTION

An endoscope device for diagnosing a lesion within a living body has been widely known. For example, a fluorescent endoscope device has been in practical use wherein excitation lights are irradiated onto a tissue surface of a living body, a fluorescent material contained in the living tissue is excited, and fluorescence emitted from the living tissue is imaged so as to obtain a fluorescent image. Such a fluorescent endoscope device may be used for diagnosing a lesion in the living tissue based on information contained in an acquired image.

When excitation lights are irradiated onto the surface of a living tissue and auto-fluorescence from the surface of the living tissue is detected, it is known that the intensity emitted by normal tissue is different from the intensity emitted by lesion tissue. Analysis of the fluorescent intensity distribution obtained from the auto-fluorescent image of a living tissue containing a lesion tissue region enables segmentation of the lesion tissue region and the normal tissue region. The living tissue shows a layer structure in which collagen or elastin, each of which generates auto-fluorescence, is primarily contained in the sub-mucosal layer. When the structure of the tissue of a mucous membrane that is situated in the upper layer of the sub-mucosal layer changes due to a lesion, the auto-fluorescence of the collagen or elastin is greatly affected and is attenuated before it reaches the superficial portion of the mucous membrane. Consequently, detection of the fluorescent intensity in a wavelength range of 420 nm-600 nm, which region includes the main auto-fluorescent wavelengths of collagen or elastin, enables information to be acquired that may be used for identifying a lesion tissue region that has developed in the mucosal layer.

It also is known that porphyrin, which is an organic compound that exists naturally within a living body, tends to accumulate in a tumor. The porphyrin, when excited using excitation light in the visible wavelength range from blue to green in a manner similar to that of collagen or elastin, generates auto-fluorescence having a peak wavelength in the vicinity of 630 nm, so the detection of fluorescence within an extremely narrow band of wavelengths that includes 630 nm is indicative that a tumor has developed in the living tissue. It is further possible that the administration of a fluorescent drug from outside the body, such as 5ALA (5-aminolevulinic acid), results in the accumulation of porphyrin in a tumor. As described above, the detection of an auto-fluorescent spectrum from the living tissue enables the extraction of different information that is contained in each spectral range.

A method and a device for diagnosing the presence of a lesion in living tissue by utilizing auto-fluorescence of the living tissue is disclosed in, for example, U.S. Pat. No. 5,769,792. The fluorescent endoscope device disclosed in this patent enables a lesion tissue region to be clearly visualized by utilizing a fluorescent image in a spectral range where the auto-fluorescent intensity of the lesion tissue is substantially different from that of normal tissue, and by utilizing another spectral range where the intensity of auto-fluorescence in the lesion tissue is substantially equal to that of normal tissue, enabling clear identification of the lesion tissue from the surrounding normal tissue.

Further, a method for diagnosing the presence of a lesion in living tissue is known that utilizes a substance that has an affinity for lesion tissue that has developed in the living body. Initially, a fluorescent substance is administered from outside the body to a site where the existence of a lesion is suspected. After some time, the fluorescent substance selectively combines with the lesion tissue, and fluorescence from the fluorescent substance is then detected by irradiating excitation lights onto the site. Such a technique enables clear identification of a lesion tissue region that has developed in the living body. As the fluorescent substance, a fluorescent probe as disclosed in patent publications WO 2003/079015 and WO 2004/005917 may be used.

A fluorescent probe typically is composed of, on the molecular level, a portion that combines with a substance that specifically participates in a process that occurs where a lesion tissue, such as a tumor, appears and develops (hereinafter, such a substance will be referred to as a 'target substance', and a pigment for generating fluorescence. Pigments that generate fluorescence can be selected from various commercially available pigments. For example, in patent publication WO 2003/079015, a fluorescent probe is disclosed composed of pigments having excitation wavelength peak(s) and fluorescent wavelength peak(s) in the wavelength range of 600 nm-1200 nm. The fluorescent probe can be manufactured at very low cost, and the verification that such a fluorescent probe is safe to use with living body tissue has already begun.

Furthermore, in patent publication WO 2004/005917, a fluorescent probe is disclosed that generates little fluorescence before combining with a target substance but, after combining with a target substance, the chemical structure of the probe changes so that the probe then generates a substantial fluorescence. Since the fluorescent probe generates a substantial fluorescence only when combined with a target substance, the accuracy of detecting a lesion can be improved by utilizing such a fluorescent probe. In addition, the fluorescent probe can be designed to selectively combine with only a specific target substance so that the selection of a target substance that has characteristics unique to a lesion enables the useful analysis and diagnosis of specificity in the lesion (for example, whether the lesion is cancerous).

BRIEF SUMMARY OF THE INVENTION

The present invention relates to a fluorescent endoscope device that irradiates excitation lights to a living body, and that then images fluorescence generated by the excitation lights so as to obtain a fluorescent image. More particularly, it relates to a fluorescent endoscope device that, with one observation, can acquire at least two types of information, and processes the information into an image useful for diagnosis so as to distinguish with high accuracy a lesion, even a lesion which has little structural change from that of normal living tissue.

BRIEF DESCRIPTION OF THE DRAWINGS

The present invention will become more fully understood from the detailed description given below and the accompanying drawings, which are given by way of illustration only and thus are not limitative of the present invention, wherein:

FIGS. 9A-9F are various diagrams that are used in describing the basic operation of the fluorescent endoscope device of the present invention;

DETAILED DESCRIPTION

Figure 1:
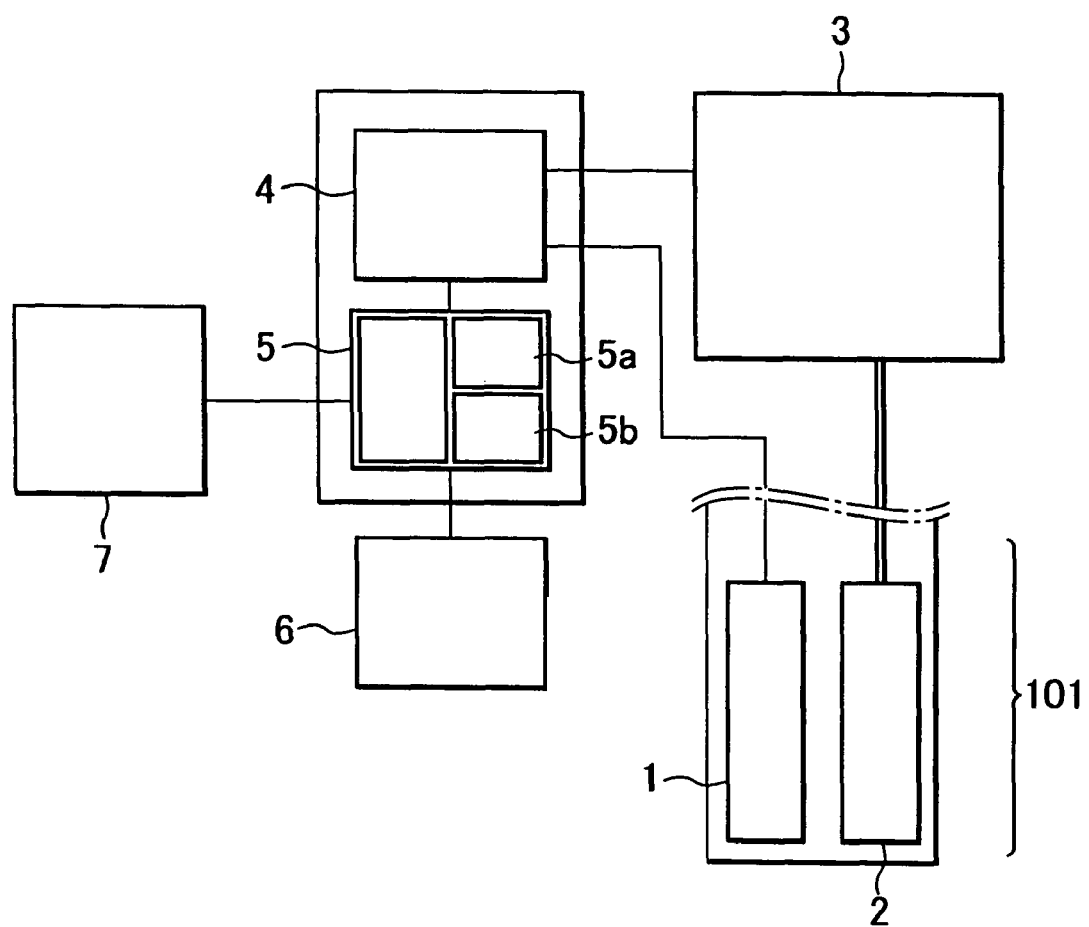
FIG. 1 illustrates the basic construction of a fluorescent endoscope device according to the present invention.

When a lesion that has developed in a living tissue is diagnosed using endoscope images, the more information regarding the lesion that is contained in the images acquired by the endoscope, the greater the likelihood that an accurate diagnosis can be provided. Therefore, it is desirable that a fluorescent endoscope device be equipped so that it can provide both a function to acquire an auto-fluorescent image from the lesion tissue in the visible wavelength region, and a function to acquire a fluorescent image having wavelengths in the region from red to near-infrared from a fluorescent probe that has been administered previously and has combined with the lesion tissue in the region. Further, it is desirable to provide a function for utilizing information regarding the lesion contained in each fluorescent image and to process the information into images useful for diagnosis.

However, in the conventional fluorescent endoscope device disclosed in U.S. Pat. No. 5,769,792, it is impossible to acquire the above-mentioned information from various fluorescent substances and to process this information so as to create an image. Further, in the patent publications WO 2003/079015 and WO 2004/005917, even though the structure of a fluorescent probe and the procedures to introduce the fluorescent probe and to detect fluorescence are disclosed, no specific construction details of the fluorescent endoscope device for the detection and analysis of the fluorescence are disclosed.

A fluorescent endoscope device that can acquire, using a single observation, several types of information by which to distinguish a lesion and that can process the information into an image useful for diagnosis, and that can enable one to diagnose with high accuracy even a lesion as occurs with an early stage of cancer that exhibits little structural change from that of normal living tissue will now be further described.

It has already been described that, in the visible wavelength region, the detection of an auto-fluorescent spectrum of lesion tissue in different wavelength ranges enables the extraction and utilization of different information contained in each spectral range, and in the spectral region from red to near-infrared wavelengths, the utilization of a fluorescent probe which can be designed to selectively acquire and combine with a specific target substance enables the fluorescent probe to be useful for the analysis and diagnosis of, for example, whether the lesion is cancerous.

The fluorescent endoscope device of the present invention is constructed so that, with one observation, a process to acquire an auto-fluorescent image of a lesion tissue and another process to acquire a fluorescent image generated by combining a fluorescent probe with a substance that distinguishes the lesion, are executable. Furthermore, the fluorescent endoscope device of the present invention is constructed to: (1) extract information that is unique to the lesion using multiple images that have been acquired in each process; (2) process the multiple images into a desired information format; and (3) re-structure a fluorescent image that is useful for diagnosis.

The basic construction of a fluorescent endoscope device according to the invention is illustrated in FIG. 1. An imaging unit 1 and an illumination unit 2 are arranged in an insertion end 101. The illumination unit 2 is connected to a light source unit 3 via an optical transmission means, such as a light guide, and an illumination light that is supplied from the light source unit 3 is irradiated onto a surface of a living tissue. The light source unit 3 is constructed so that multiple excitation lights having different wavelength components can be generated using wavelengths from at least the visible wavelength region to the infrared wavelength region. The imaging unit 1 and the light source unit 3 are connected to a control unit 4. The control unit 4 controls the timing that the light source unit 3 generates the excitation light and supplies the generated excitation light to the illumination unit 2, and the timing that the imaging unit 1 acquires the fluorescent image from the living tissue surface. In this manner a fluorescent image from the surface of the living tissue is formed by the imaging unit 1, image signals are acquired by the imaging unit 1, and the image signals are processed by an image processing unit 5. The image processing unit 5 is equipped with a memory circuit 5a to temporarily store the image signals as data and an operation circuit 5b that performs an operation required for image processing based on the data stored in the memory circuit 5a. Further, an external recording device 6, such as a DVD or HDD, is connected to the image processing unit 5. This enables the image signals generated by the imaging unit 1 and the image data processed by the image processing unit 5 to be recorded in an external recording device 6. The data recorded in the external recording device 6 may be read by the image processing unit 5 and processed. The fluorescent image that has been processed by the image processing unit 5 may then be displayed on a TV monitor 7.

A fluorescent probe applicable to the diagnosis of a lesion tissue using the fluorescent endoscope device is constructed using pigments that absorb light having a wavelength of 500 nm or longer and that then emit fluorescence. Commercially available pigments that can be used include, for example, dicarbocyanine pigments Cy5 and Cy5.5 manufactured by Amersham Bioscience, tricarbocyanine pigment Cy7 manufactured by Amersham Bioscience, or ALEXA FLUOR 700 manufactured by Invitrogen. The primary absorption wavelength range and fluorescent wavelength range of each of these pigments are as shown in Table 1 below.

TABLE 1

| Pigment | Absorption wavelength (nm) | Fluorescent wavelength (nm) |
|---|---|---|
| Cy5 | 580-660 | 640-680 |
| Cy5.5 | 620-700 | 670-710 |
| ALEXA FLUOR 700 | 650-720 | 700-740 |
| Cy7 | 650-770 | 760-800 |

According to Table 1, the primary absorption wavelength ranges of these four pigments substantially overlap. However, it is clear that the fluorescent wavelength ranges differ enough to be detectable by separating each fluorescent wavelength range. In other words, the selection of an appropriate wavelength light from the red wavelength range enables simultaneous excitation of the pigments and the individual detection of fluorescence generated by the pigments. Therefore, if a plurality of fluorescent probes are made by using the above mentioned pigments, which selectively combine with different target substances that specifically participate in a process that occurs where there is lesion tissue (for example, a substance that occurs in a malignant lesion, and a substance associated with an active growth area of a lesion), these probes may be excited with a common excitation light and generate a plurality of fluorescent lights of different wavelengths. These probes are useful for improving accuracy in diagnosing a lesion tissue with a fluorescent endoscope device.

Figure 2:
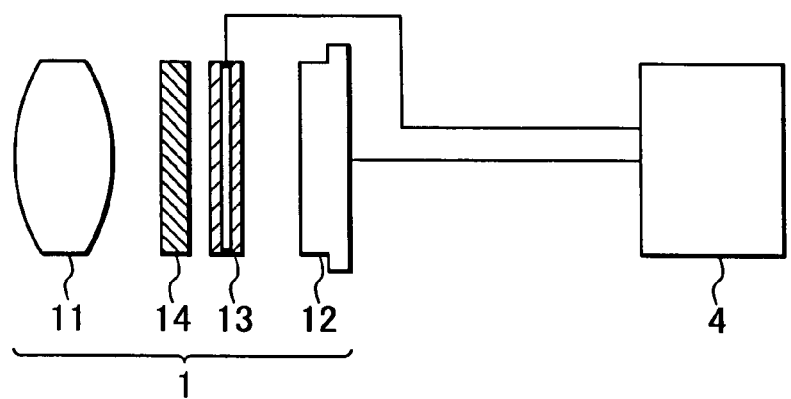
FIG. 2 illustrates an example of the construction of an imaging unit 1.

FIG. 2 shows a construction example of an imaging unit 1. In order for multiple fluorescent probes to be excited and their fluorescence separately detected, the imaging unit 1 is equipped with an objective optical system 11, a photo detector 12 (which serves as an image pickup device) and a variable transmittance optical element 13. The variable transmittance optical element 13 may be located between the surface of the objective optical system 11 that is nearest the image side and the acceptance surface of the photo detector 12. Further, an optical filter 14 for shielding light which excites the fluorescent probes may be arranged between the object-side-surface of the objective optical system 11 and the variable transmittance optical element 13. In the imaging unit 1 shown in FIG. 2, the variable transmittance optical element 13 is an etalon. By changing the air gap spacing of the etalon, the peak transmittance wavelength that is transmitted by the etalon may be changed.

The construction of the imaging unit 1 is such that the air gap spacing of the etalon is controlled by the control unit 4 in synchronization with the irradiation periods of the excitation lights. When lights enabling simultaneous excitation, for example, of three fluorescent probes are irradiated onto the surface of the living body tissue via the illumination unit 2, the etalon is controlled to have at least three different transmitted light wavelength ranges during the irradiation period of the excitation lights.

Meanwhile, in the case of exciting an auto-fluorescent substance (i.e., a fluorescent substance that naturally exists within a living body), a wavelength range of 500 nm or shorter is used. For example, light of 405 nm can excite collagen or elastin that naturally occurs in the sub-mucosal layer of living tissue, and such light can simultaneously excite porphyrin, which is an organic compound that occurs naturally within a living body. Collagen and elastin mainly generate fluorescence within the wavelength range of 420 nm-600 nm, and porphyrin generates fluorescence having a wavelength of 630 nm, making it possible to separately detect the fluorescence when using the imaging unit 1 shown in FIG. 2.

Fluorescence from collagen or elastin and fluorescence from porphyrin contain different information regarding a lesion, that is, the auto-fluorescent light having different wavelengths contain different information regarding a lesion. Therefore, by using both an observation of the auto-fluorescence and an observation that uses multiple fluorescent probes in combination, the total information obtained increases as compared with the information obtained using a single fluorescent observation. This enables an outstanding improvement in the accuracy of the diagnosis of lesion tissue. For example, in cancer tissue that has only recently developed in a living body and which has not yet grown, it is believed that there are almost no histological structural differences from that of the peripheral normal tissue. Consequently, it is rare that any noticeable difference appears in the auto-fluorescent intensity distribution on the surface of the living body tissue. Thus, it is very easy to not notice a cancer when using a conventional method for observing the auto-fluorescent intensity distribution. However, if use is made of fluorescent probes that combine with multiple substances that exist in the cancer tissue, the acquisition of information unique to the cancer tissue and the processing of this information into an image useful for cancer diagnosis, as in the present invention, enables a drastic reduction in the possibility of an observer not noticing a cancer.

The fluorescent probes are composed of pigments for absorbing a wavelength of light of 500 nm or longer and that then generate a fluorescence. Fortunately, the fluorescent probes will never be excited by the excitation light used for observations of auto-fluorescence. Further, an auto-fluorescent substance within a living body absorbs almost no light of wavelengths of 500 nm or longer, and thus the fluorescence from auto-fluorescent substances will never become noise or otherwise become an obstruction of the observation light when utilizing fluorescent probes. The clear separation of wavelengths between light used to excite fluorescent probes and light used to excite auto-fluorescent substances enables the fluorescence from fluorescent probes and the fluorescence from auto-fluorescent substances to be detected with excellent contrast.

Figure 3:
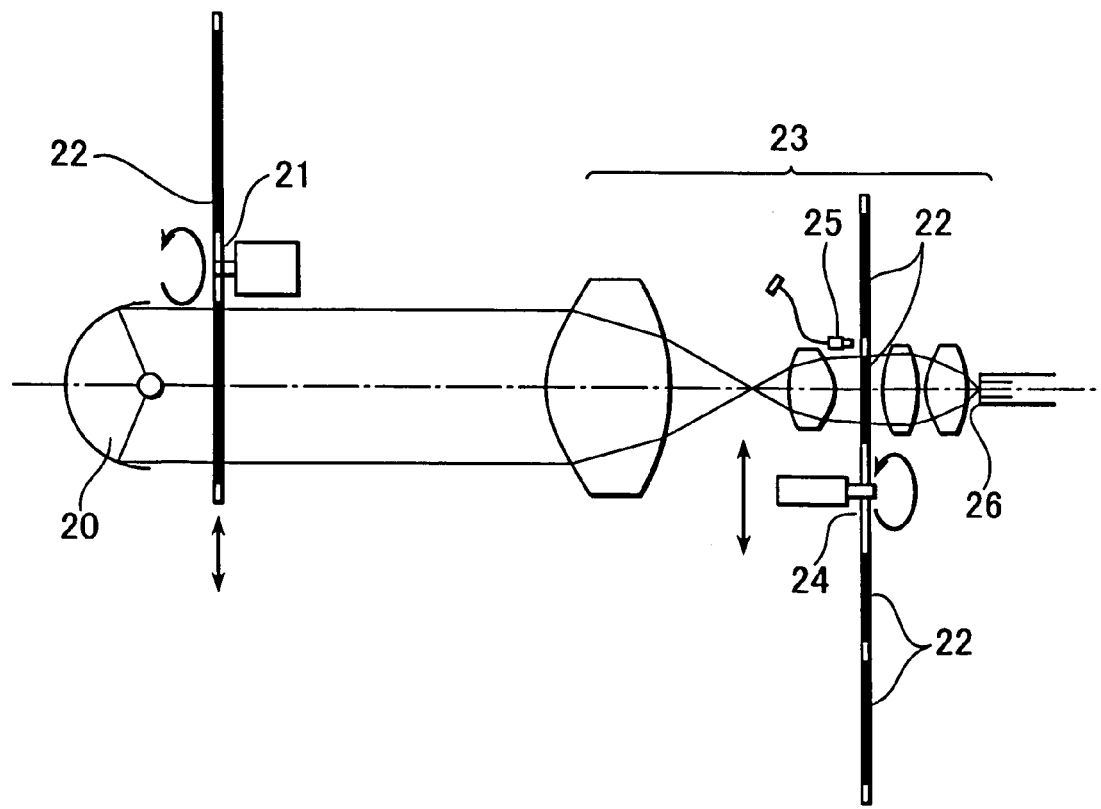
FIG. 3 illustrates an example of the construction of a light source unit 3.

FIG. 3 shows an example of the construction of a light source unit 3. A lamp 20 is a discharge-type xenon lamp. In order for multiple illumination lights with different wavelength ranges to be selectable, optical filters 22 are arranged in the turret 21 and in the rotating disc 24 that are positioned in the optical path from the lamp 20 to the light guide incidence end 26 of the endoscope.

Figure 4A:
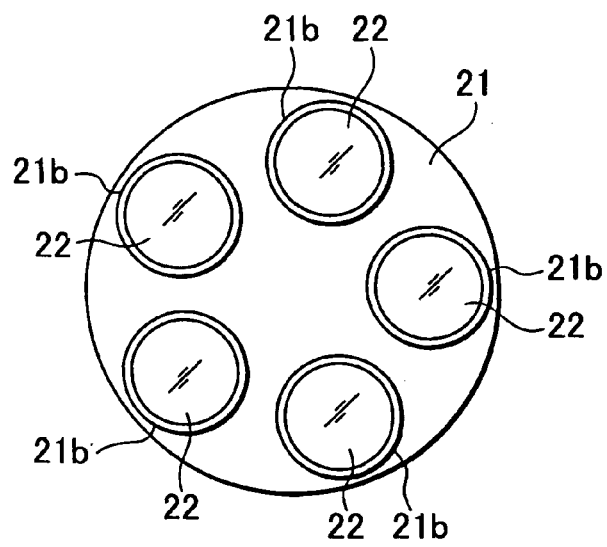
FIGS. 4A, 4B and 4C illustrate examples of the construction of a turret 21 and a rotating disc 24 that may be arranged in the light source unit 3, with FIGS. 4A and 4B being axial and side views, respectively, of the turret 21, and FIG. 4C being an axial view of the rotating disc 24.
Figure 4B:
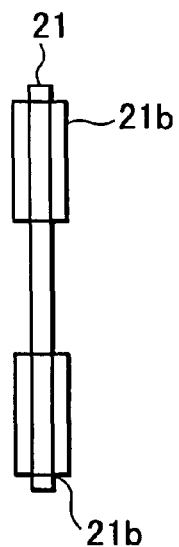

Referring to FIGS. 4A and 4B, in the turret 21, at least five filter holders 21b are established so as to be concentric to the substrate center of the turret 21, and one or multiple optical filters 22 are housed in each of the filter holders 21b. The filter holders 21b may be arranged in the turret 21 as shown in FIGS. 4A and 4B, with FIG. 4A being an axial view of the turret 21 and FIG. 4B being a side view of the turret 21. By rotating the turret 21 about its center, the optical filters 22 housed in the filter holders 21b may be selectively inserted into the optical path.

Figure 4C:
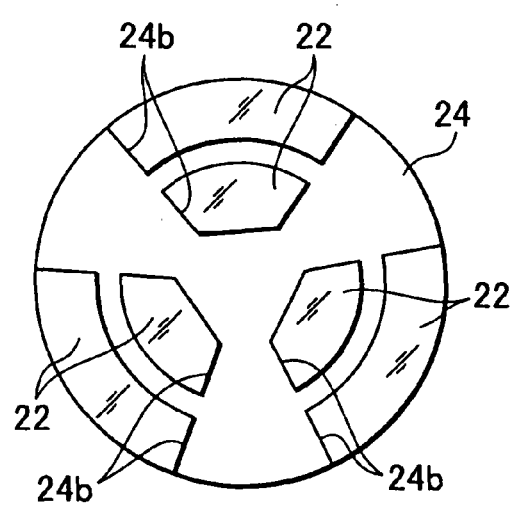

Referring to FIG. 4C, in the rotating disc 24, windows 24b are established so as to be concentric relative to the substrate center at spaced intervals, and the optical filters 22 are adhered and fixed to the windows 24b. The windows 24b are established at outer and inner regions of the disc substrate. FIG. 4C is an axial view of the rotating disc 24 and shows the construction of the windows 24b arranged in the rotating disc 24. The rotating disc 24 rotates at a constant speed about its center. Further, the rotating disc 24 can be moved orthogonally relative to the optical axis of the collector optical system 23 by a rotating disc movement mechanism (not shown).

The movement of the rotating disc 24 to an appropriate position enables the selective production of the following three illumination states:

illumination state 1—a state wherein a series of optical filters 22 that are arranged in an outer region of the rotating disc 24 are sequentially inserted into the optical path and illumination is repeatedly performed;

illumination state 2—a state wherein another series of optical filters 22 arranged in an inner region of the rotating disc 24 are sequentially inserted into the optical path and illumination is repeatedly performed; and illumination state 3—a state wherein the rotating disc 24 is moved out of the optical path and illumination is performed.

Therefore, the combination of the arrangement of the optical filters in the rotating disc 24 and in the turret 21 and the positioning of these components in the optical path enables the selection of multiple different illumination states.

Figure 5A:
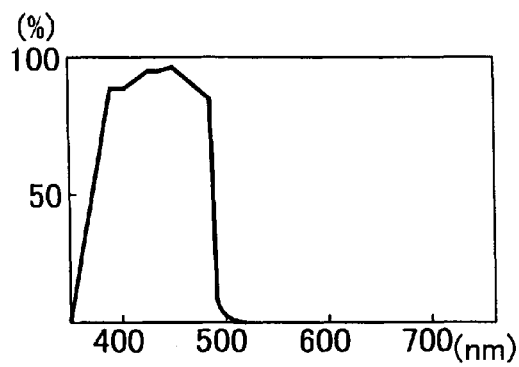
FIGS. 5A-5F illustrate the spectral transmittance (more specifically, the % transmittance versus wavelength, in nm) of various optical filters 22 that may be arranged in the turret 21 and the rotating disc 24.
Figure 5B:
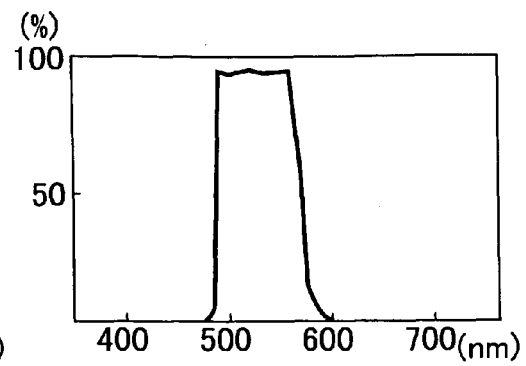
Figure 5C:
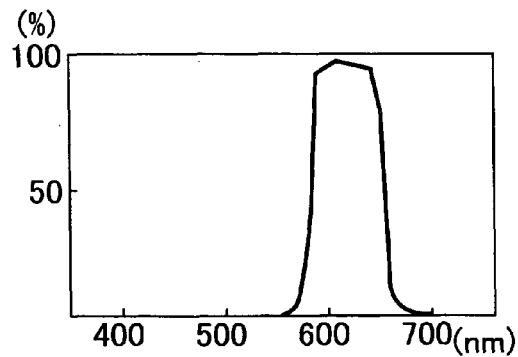
Figure 5D:
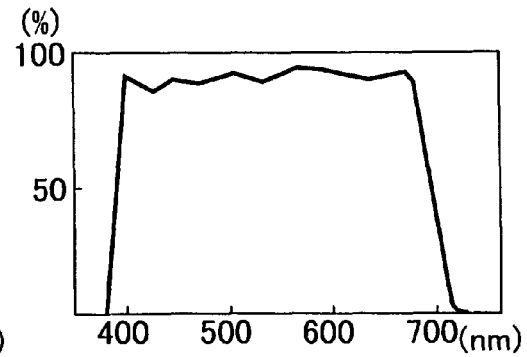
Figure 5E:
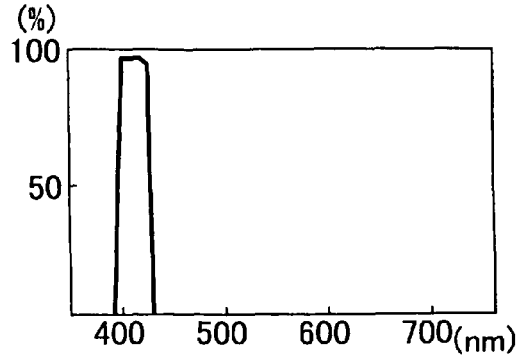
Figure 5F:
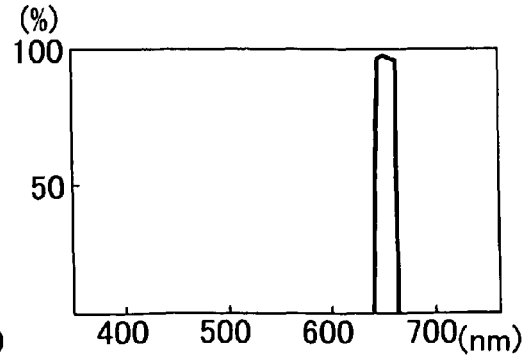

FIGS. 5A-5F show examples of the spectral transmittance of various optical filters 22 that may be arranged in the windows of the turret 21 and of the rotating disc 24. In FIGS. 5A-5F, % transmittance is plotted on the vertical axis (i.e., the ordinate) and wavelength, in nm, is plotted on the horizontal axis (i.e. the abscissa). FIGS. 5A-5C show the spectral transmittance of the optical filters 22 arranged in the inner region of the rotating disc 24. FIG. 5D shows the spectral transmittance of each of the optical filters 22 arranged in windows of the turret 21; and FIGS. 5E and 5F show the spectral transmittance of respective optical filters 22 that may be arranged in windows in the outer region of the rotating disc 24. Further, of the respective spectral transmittances of the optical filters 22 shown in FIGS. 5A-5F, the wavelength ranges where the % transmittance T is 50% or greater are as shown in Table 2. The % transmittance T is given by the following equation:

$$T = (IL1/IL2) \times 100\%$$

where

IL1 is a total amount of light incident on the filter 22 at a wavelength $\lambda$, and IL2 is a total amount of light that transmits through the filter at the wavelength $\lambda$.

TABLE 2

| FIG. | Wavelength range, in nm, where transmittance T is 50% or greater |
|---|---|
| 5A | 380-485 |
| 5B | 490-570 |
| 5C | 585-660 |
| 5D | 390-690 |
| 5E | 400-430 |
| 5F | 670-690 |

When fluorescent observation of living body tissue is performed, the turret 21 rotates and optical filters having a spectral transmittance as shown in FIG. 5D are inserted in the optical path. Further, the rotating disc 24 moves in a plane that is generally normal to the optical axis so that optical filters in the outer region of the rotating disc 24 are inserted in the optical path. The rotating disc 24 rotates at a constant speed, and the optical filters with the spectral transmittances as shown in FIGS. 5E and 5F are sequentially inserted into the optical path. As a result, narrow-band wavelength region A (see FIG. 6) having a wavelength shorter than 500 nm that excites the auto-fluorescent substances and a narrow-band wavelength region B (see FIG. 6) having a wavelength longer than 500 nm that excites the fluorescent probes are repeatedly irradiated onto the living body tissue via the illumination unit 2 for a given length of time. The optical filters arranged in the inner region of the rotating disc 24 are used when R, G and B lights for normal color image observation are generated. Consequently, the light source unit 3 can select two modes, an excitation light generation mode for fluorescent image observation and an RGB light generation mode for normal color image observation.

The transmittance wavelength range of the optical filters for fluorescent image observation is extremely narrow compared to that for normal color image observation, and is established at 30 nm or less. Consequently, the brightness of the excitation lights on the surface of the living body tissue becomes darker than an illumination light for normal color image observation. In order to improve the brightness of the excitation lights, it is preferable that the lighting current of the lamp 20 be increased compared to that used for the illumination during normal color image observation. Thus, the intensity of light emitted from the lamp 20 is increased.

Figure 6:
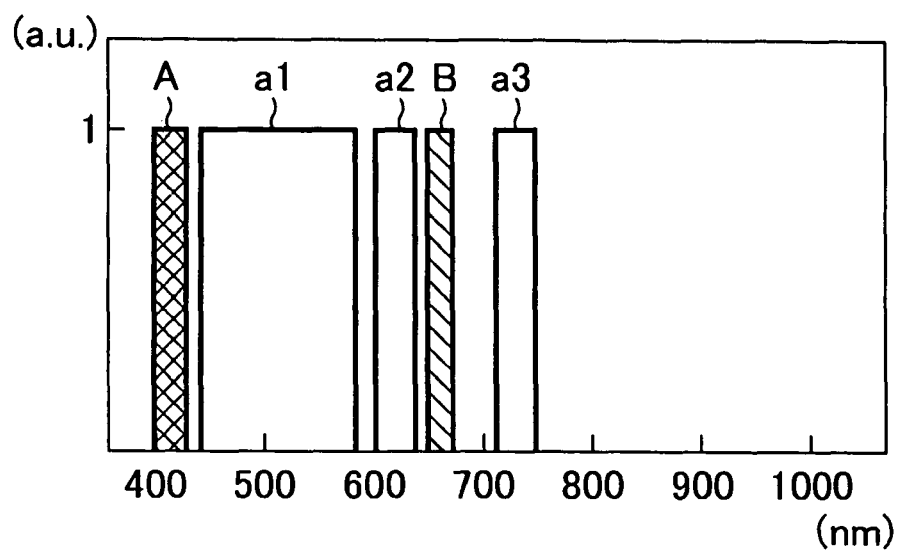
FIG. 6 is a conceptual illustration that shows the relationship between the wavelength ranges of excitation lights generated by the light source unit 3 and the wavelength range of fluorescence detected by the imaging unit 1.

FIG. 6 is a conceptual illustration that shows the relationship between the wavelength range of excitation lights generated by the light source unit 3 and the wavelength range of fluorescence detected by the imaging unit 1. The vertical axis indicates the intensities of the excitation lights and the fluorescent lights in arbitrary units, and the horizontal axis indicates the wavelength, in nm. In actuality, the average intensity of the excitation lights is approximately 100 to 500 times the intensity of the peak fluorescent intensity. However, in order to show the relationship between the excitation lights and the fluorescent lights, the display scale of the excitation light intensity has been normalized to 1 and they are shown together in one figure. In the below-mentioned embodiments, when the relationship between the excitation light and the fluorescent light is shown, a similar conceptual illustration will be shown and described.

Referring to FIG. 6, the irradiation using the narrow-band wavelength region A for exciting the auto-fluorescent substances in a living body for a given length of time results in the excitation of collagen or elastin that is naturally occurring in the sub-mucosal layer of living body tissue and results in the generation of fluorescence in the wavelength region a1. Simultaneously, the irradiation using the narrow-band wavelength region A results in the excitation of porphyrin, which is an organic compound that is naturally occurring within the living body, and results in the generation of fluorescence in the wavelength region a2. Further, the irradiation using the narrow-band wavelength region B for exciting fluorescent probes that have been previously administered to a patient results in the excitation of the fluorescent probes that have combined with lesion tissue of the patient and the generation of fluorescence in the wavelength region a3.

Figure 7:
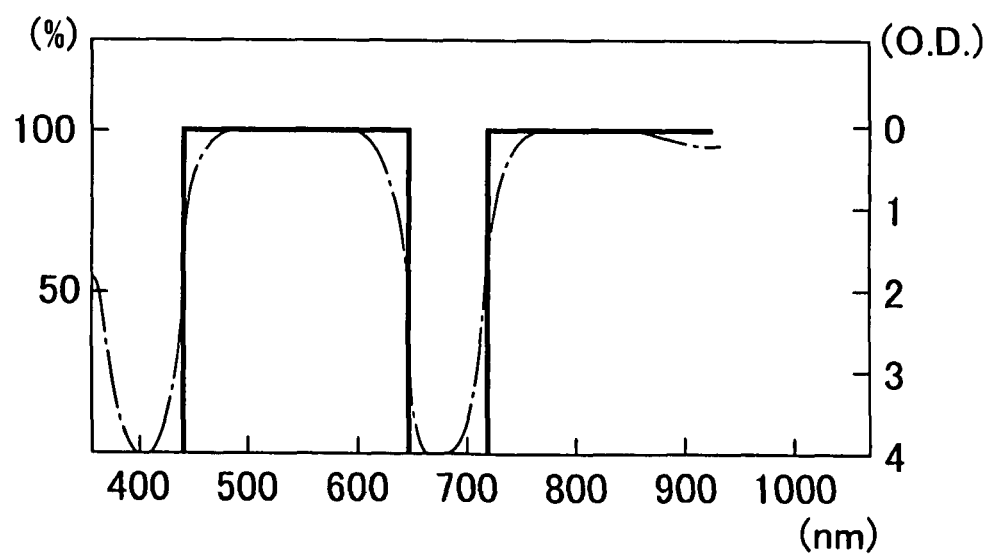
FIG. 7 shows optical characteristics of an excitation light blocking filter, such as the excitation light cut-off filter 14 that is arranged in the imaging unit 1 illustrated in FIG. 2.

FIG. 7 shows optical characteristics of an excitation light cut-off filter 14 that may be arranged in the imaging unit 1. In FIG. 7, the solid line indicates the ideal % transmittance property of the excitation light cut-off filter 14 for the light ray incident on the filter surface at an angle of 0°, for which the left-side vertical scale applies. On the other hand, the chain line indicates the best optical density property of the excitation light cut-off filter 14 for the light ray incident on the filter surface at an angle of 0°, which may be realized as an actual filter. The right-side vertical scale applies to the optical density property. That is, the ideal state is shown by the % transmittance. The actual state is shown by the optical density. Optical density is defined as set forth in Equation (A) below:

$$O.D.=\log_{10}(I/I')$$ Equation (A)

where
I is the intensity of light that is incident, and
I' is the intensity of light that is transmitted.

The horizontal axis in FIG. 7 represents the wavelength, in nm.

The excitation light cut-off filter 14 is arranged for preventing the narrow-band wavelength region A that is used for exciting the auto-fluorescent substances and the narrow-band wavelength region B that is used for exciting the fluorescent probes from reaching the surface of the photo detector 12. Thus, the excitation light cut-off filter 14 prevents the reduction of contrast in the fluorescent image that would otherwise occur if the excitation light cut-off filter 14 were not present. Consequently, in the wavelength ranges of the narrow-band wavelength regions A and B, the excitation light cut-off filter 14 is determined to have an optical density such that the sum of the optical density ODF of the excitation light cut-off filter 14 that is arranged in the optical path of the imaging unit 1 and the optical density ODE of the etalon 13 is 4 or greater, thereby enabling the average intensity of the excitation lights on the photo detector 12 to be 1/20 or less than that of the peak intensity of the fluorescence, thereby providing a fluorescent image having excellent contrast.

Figure 8A:
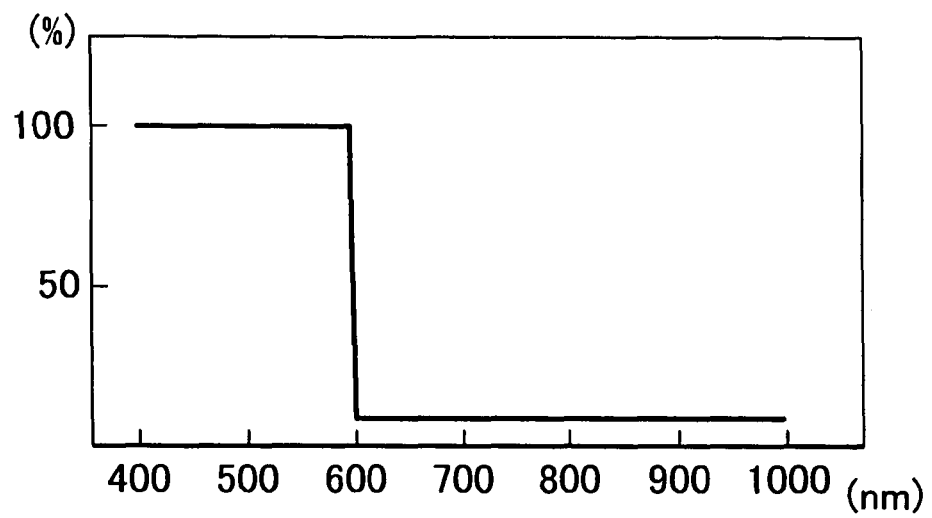
FIGS. 8A and 8B illustrate the spectral transmittance (in % transmittance versus wavelength, in nm) of an etalon 13 that includes an air gap spacing, with FIG. 8A showing the spectral transmittance of each of the two surfaces of the etalon 13, which is opposite to each other with an air gap spacing there between, and FIG. 8B showing the spectral transmittance of the etalon 13 wherein a peak transmittance wavelength changes with the air gap spacing.
Figure 8B:
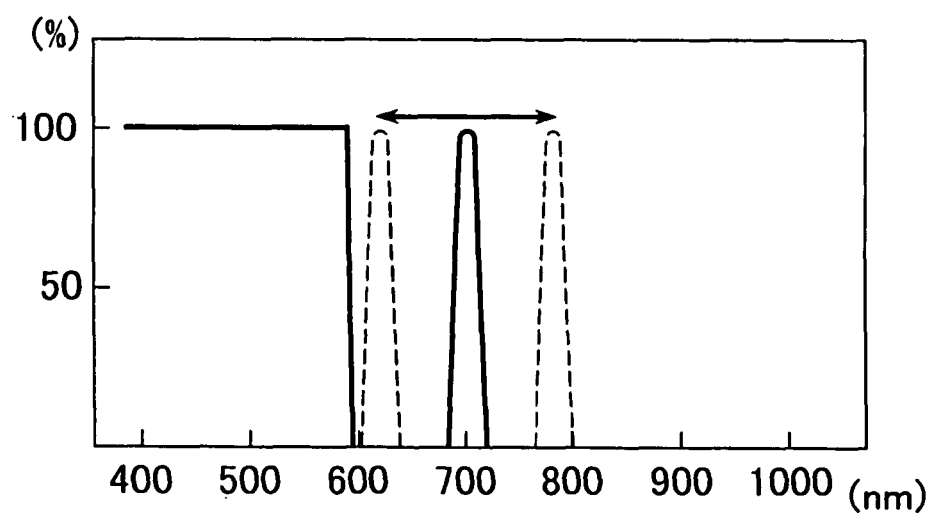

The etalon 13 has a first wavelength transmission range in which, even if the air gap spacing is changed, the average % transmittance is maintained at 50% or greater for incident wavelengths less than 600 nm, and a second wavelength transmission range in which, for incident wavelengths of 600 nm or longer, the peak transmittance wavelength increases when the air gap spacing increases to thereby scan the peak transmittance wavelength of the etalon. The term "average % transmittance" is herein defined as the numerical average of the % transmittance as measured over a specified wavelength range. FIGS. 8A and 8B illustrate the average % transmittance (as measured on the vertical axis) versus the wavelength, in run (as measured on the horizontal axis), of an etalon 13 that includes an air gap spacing, with FIG. 8A showing the average % transmittance of each of the two surfaces of the etalon 13, which is opposite to each other with an air gap spacing there between, and FIG. 8B showing the average % transmittance of the etalon 13 wherein the peak transmittance wavelength changes with air gap spacing.

As can be seen from FIG. 8A, the average % transmittance of each of the two surfaces of the etalon 13 is established at a value less than 50% in the wavelength range longer than 600 nm (i.e., λ>600 nm), and at a value of 50% or more in the wavelength range of 600 nm or shorter (i.e., λ≦600 nm). As can be seen from FIG. 8B, even though the air gap spacing has been changed, the average % transmittance of the etalon remains at a value of 50% or greater for wavelengths 600 nm or shorter, but the peak transmittance wavelength changes with air gap spacing for wavelengths longer than 600 nm. As a result, the etalon 13 can be constructed to stably transmit light in a first wavelength transmission range (λ≦600 nm) regardless of the air gap spacing; and, at the same time, to enable the scanning of the transmittance peak wavelength utilizing an interference effect in a second wavelength transmission range (λ>600 nm).

A basic operation of the fluorescent endoscope device in the case of executing a process to acquire an auto-fluorescent image of a lesion tissue, and another process to acquire a fluorescent image generated by fluorescent probes combining with a substance which distinguishes the lesion tissue will now be described with reference to FIGS. 9A-9F. FIG. 9A is a conceptual illustration used in explaining the relationship between the wavelength range of excitation lights generated by the light source unit 3 and the wavelength range of fluorescence detected by the imaging unit 1, and is similar to FIG. 6. As before, the vertical axis indicates the intensity of excitation lights and fluorescence in arbitrary units, and the horizontal axis indicates the wavelength in nm. FIGS. 9B and 9C show the spectral transmittance of the etalon, with the vertical axis in each figure indicating the % transmittance and the horizontal axis indicating the wavelength, in nm. FIGS. 9D-9F show the intensity of light that is sequentially received by the photo detector that acquires an image due to the light transmitted by the etalon, and the timing of the irradiations onto the etalon, when the etalon has the transmission characteristic shown in the figure to the left. Thus, FIG. 9C is illustrated twice. The vertical axis in each of FIGS. 9D-9F indicates the light intensity, in arbitrary units, and the horizontal axis indicates the wavelength, in nm.

Referring to FIG. 9A, a case is illustrated wherein the irradiation, for a given length of time, of the narrow-band wavelength region A for exciting auto-fluorescent substances that are naturally occurring in a living body results in the generation of fluorescence in the wavelength region a1 from collagen or elastin and the generation of fluorescence in the wavelength region a2 from porphyrin, and another case is illustrated wherein the irradiation, for a given length of time, of the narrow-band wavelength region B for exciting fluorescent probes that have been administered to the living body results in the generation of fluorescence in the wavelength region a3 from the fluorescent probes that have combined with lesion tissue.

While the light source unit 3 in the fluorescent endoscope device generates the narrow-band wavelength region A, the etalon 13 is adjusted to be in one of two states according to control signals transmitted from the control unit 4 in the fluorescent endoscope device, as follows:

state 1—a state transmissive to the wavelength ranges as illustrated in FIG. 9B and, since fluorescent light in the wavelength ranges a1 and a2 is generated by the excitation light in the narrow-band wavelength region A, fluorescence in both wavelength ranges a1 and a2 is received by the photo detector, as indicated in FIG. 9D;

state 2—a state transmissive to the wavelength ranges as illustrated in FIG. 9C, which includes the wavelength ranges a1 and a3, but no light in the wavelength range a3 is generated by the excitation light in the narrow-band wavelength region A. Therefore, fluorescence only in the wavelength region a1 is received by the photo detector, as illustrated in FIG. 9E.

Thus, while the etalon 13 is set to state 1, fluorescence in the wavelength regions a1 and a2 (as illustrated in FIG. 9D) is received by the photo detector 12. When the etalon 13 is set so as to be in state 2, only fluorescence in the wavelength region a1 is received by the photo detector 12, as illustrated in FIG. 9E.

While the light source unit 3 in the fluorescent endoscope device generates the narrow-band wavelength region B, the etalon 13 is set by control signals transmitted from the control unit 4 so as to be in the following state:

state 2—a state transmissive to the wavelength ranges as illustrated in FIG. 9C, which includes the fluorescent wavelength ranges a1 and a3, but no light in the wavelength range a1 is generated by the excitation light in the narrow-band wavelength region B, so only the fluorescent wavelength region a3 is received by the photo detector 12, as illustrated in FIG. 9F.

Thus, state 2 of the etalon is transmissive to light in the wavelength regions a1 and a3, and there are three different illumination periods A1, A2, and B1 which correspond to incident light being received by the photo detector 12 having wavelengths as illustrated in FIGS. 9D, 9E and 9F, respectively. These three illumination periods result from the light source unit 3 successively generating light in narrow-band wavelength regions A and B in the two etalon states being controlled.

Figure 10:
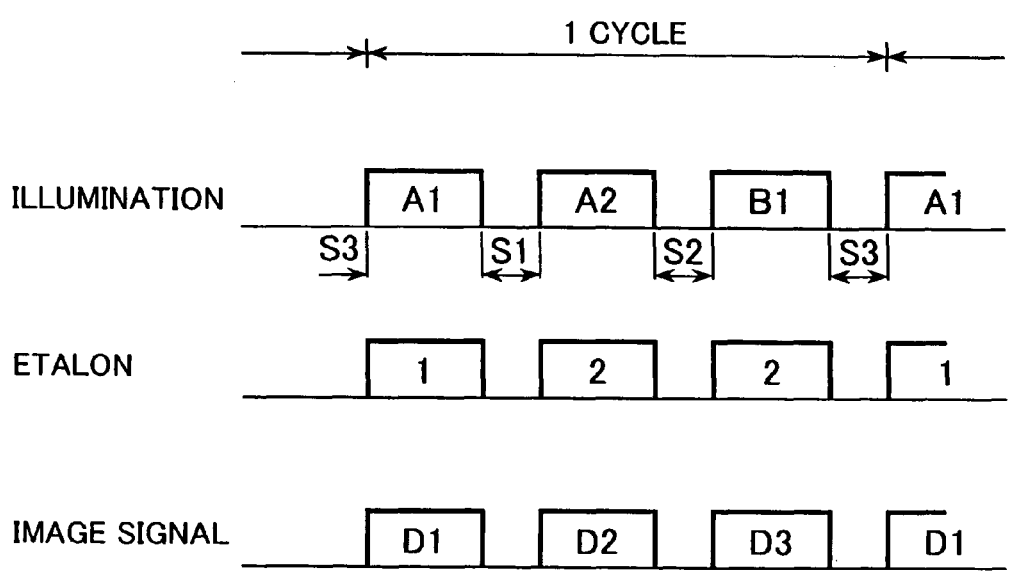
FIG. 10 is a timing chart showing the timing relationships during operation of the fluorescent endoscope device of the present invention for one cycle of the rotating disc 24, including the illumination periods, the etalon states, and the image signals acquired by the imaging unit.

FIG. 10 is a timing chart that shows the timing of the illumination periods, the etalon states, and the obtaining of image signals by the imaging unit 1. During illumination period A1 when the illumination unit 2 in the fluorescent endoscope device irradiates the narrow-band wavelength region A, the etalon 13 is set to be in state 1. As a result, the imaging unit 1 in the fluorescent endoscope device acquires image signals D1 containing fluorescent components in the wavelength regions a1 and a2. The image signals D1 are then read out during the next period S1 when the excitation light is shielded, and are stored in a memory circuit 5a in the image processing unit 5 of the fluorescent endoscope device. Further, during a second illumination period A2 when the illumination unit 2 irradiates the narrow-band wavelength region A, the etalon 13 is set to be in state 2. As a result, the imaging unit 1 acquires image signals D2 containing fluorescent components in the wavelength region a1. The image signals D2 are then read out during the next period S2 when the excitation light is shielded and are stored in the memory circuit 5a of the image processing unit 5. Further, during a third illumination period B1 when the illumination unit 2 irradiates the narrow-band wavelength region B, the etalon 13 is set so as to be in state 2. As a result, the imaging unit 1 acquires image signals D3 containing fluorescent components in the wavelength region a3. The image signals D3 are then read out during the next period S3 when the excitation light is shielded and are stored in the memory circuit 5a of the image processing unit 5.

Figure 11:
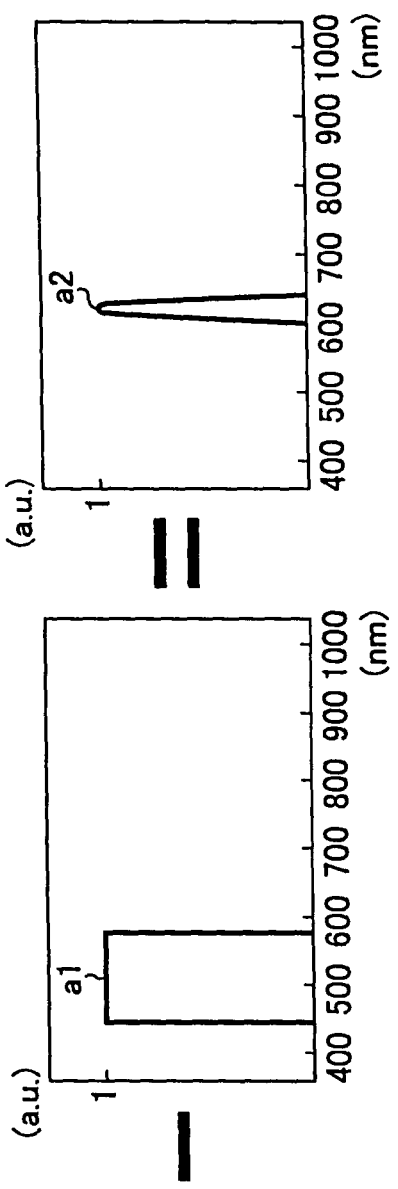
FIGS. 11A-11C are conceptual illustrations used in describing a signal processing operation using image signals D1 (illustrated in FIG. 11A), image signals D2 (illustrated in FIG. 11B), and the result (illustrated in FIG. 11C) of subtracting the image signals D2 from the image signals D1.

Considering the three illumination states as one cycle, excitation lights in the narrow-band wavelength region A and in the narrow-band wavelength region B are repeatedly illuminated onto a tissue surface of a living organism, and image processing is performed based on three types of image signals acquired during one cycle. First, an operating circuit 5b in the image processing unit 5 carries out an operation using (from among the three types of image signals) the image signals D1 and the image signals D2 that are stored while excitation light in the narrow-band wavelength region A illuminates the tissue. FIGS. 11A-11C are conceptual illustrations that will be used in describing the operation using the image signals D1 and the image signals D2, with the vertical axis indicating the signal intensity and the horizontal axis indicating the wavelength. The image signals D1 have fluorescent components in the wavelength regions a1 and a2 as shown in FIG. 11A, and the image signals D2 have fluorescent components in the wavelength region a1 as shown in FIG. 11B. By subtracting the image signals D2 from the image signals D1, new image signals E1 are generated having fluorescent components only in the wavelength region a2, as shown in FIG. 11C.

Next, color signals for color display on the screen of the TV monitor 7 are allocated to the three image signals, namely, image signals D2, image signals E1 and image signals D3. For example, when the three color signals, R, G and B, are allocated as in Table 3 below, a fluorescent image on the screen of the TV monitor 7 is color-coded according to the state of the living tissue as in Table 4 below, and is then displayed.

TABLE 3

| Image signal: | D2 | E1 | D3 |
|---|---|---|---|
| Color signal: | R | G | B |

TABLE 4

| | Displayed Color | R signal intensity | G signal intensity | B signal intensity |
|---|---|---|---|---|
| Normal tissue | Yellow | Strong | Strong | Weak |
| Inflamed tissue | Gray | Weak | Weak | Weak |
| Tumor tissue | Magenta | Weak | Strong | Strong |

The auto-fluorescence of collagen or elastin (hereinafter referred to as fluorescence F01) existing in the sub-mucosal layer of the living organism tissue is emitted from the mucosal surface through the mucosal layer. Similarly, the auto-fluorescence of porphyrin (hereinafter referred to as fluorescence F02), which is an organic compound that is naturally occurring within living organisms, is also emitted from the mucosal surface via the mucosal layer. However, when a superficial portion of the mucous membrane is inflamed, the blood flow in the superficial portion of the mucous membrane increases, the intensity of fluorescence F01 and the intensity of fluorescence F02 are attenuated, and thus the fluorescent intensity that is emitted from the mucosal surface is weakened. Consequently, the intensities of the fluorescence F01 and of the fluorescence F02 that are observed from the inflamed tissue become weaker compared to that of the fluorescence F01 and the fluorescence F02 observed from the surrounding normal tissue.

Similarly, if a tumor has developed in the mucosal tissue, the nuclei of the cells of the tumor tissue grows and/or the blood flow around the nucleus increases, resulting in blockage of the fluorescence F01 and of the fluorescence F02, and thus the intensity of the fluorescence emitted from the mucosal surface is weakened. However, porphyrin tends to greatly accumulate in the tumor, so the fluorescence F02 emitted toward the mucosal surface from tumor tissue results in supplementing the intensity of the fluorescence F02 that has been blocked by the tumor tissue. Consequently, the intensity of the fluorescence F01 observed from the tumor tissue becomes weaker as compared to that of the fluorescence F01 observed from the surrounding normal tissue. However, the intensity of the fluorescence F02 observed from the tumor tissue remains the same or becomes stronger as compared to that of the fluorescence F02 observed from the surrounding normal tissue.

Further, fluorescent probes generate fluorescence by combining with a substance that originates in tumor tissue, so fluorescence from a probe will be observed only from tumor tissue. By allocation of color signals to the three types of image signals (i.e., the image signals D2, the image signals E1 and the image signals D3), it is possible to display normal tissue in yellow, inflamed tissue of the superficial portion of the mucous membrane in gray, and tumor tissue in magenta.

In order to diagnose with high accuracy using an endoscopic observation device a lesion that exhibits only minor structural changes in a living tissue (such as a lesion in an early stage of cancer), it is desirable that the observed image on a display screen be color-coded. This, for example, enables one to clearly distinguish between the lesion portion and other regions. As mentioned above, the construction of the displayed image by utilizing the three types of image signals having individual information regarding the lesion tissue enables a clear distinction to be made between the lesion portion and other regions. In particular, at a site where it previously has been difficult to distinguish a lesion tissue using a conventional observation method, inflammation in normal tissue can now be displayed with a different color from that of lesion tissue, thereby enabling the lesion tissue to be easily identified and enabling the diagnosis accuracy to be drastically improved.

Further, the individual fluorescent image contains inherent information regarding the lesion tissue, so if an individual fluorescent image can be displayed in addition to displaying a quasi-color-coded image, diagnosis of the lesion tissue becomes easier.

Several embodiments of the invention will now be described in detail.

EMBODIMENT 1

Figure 12:
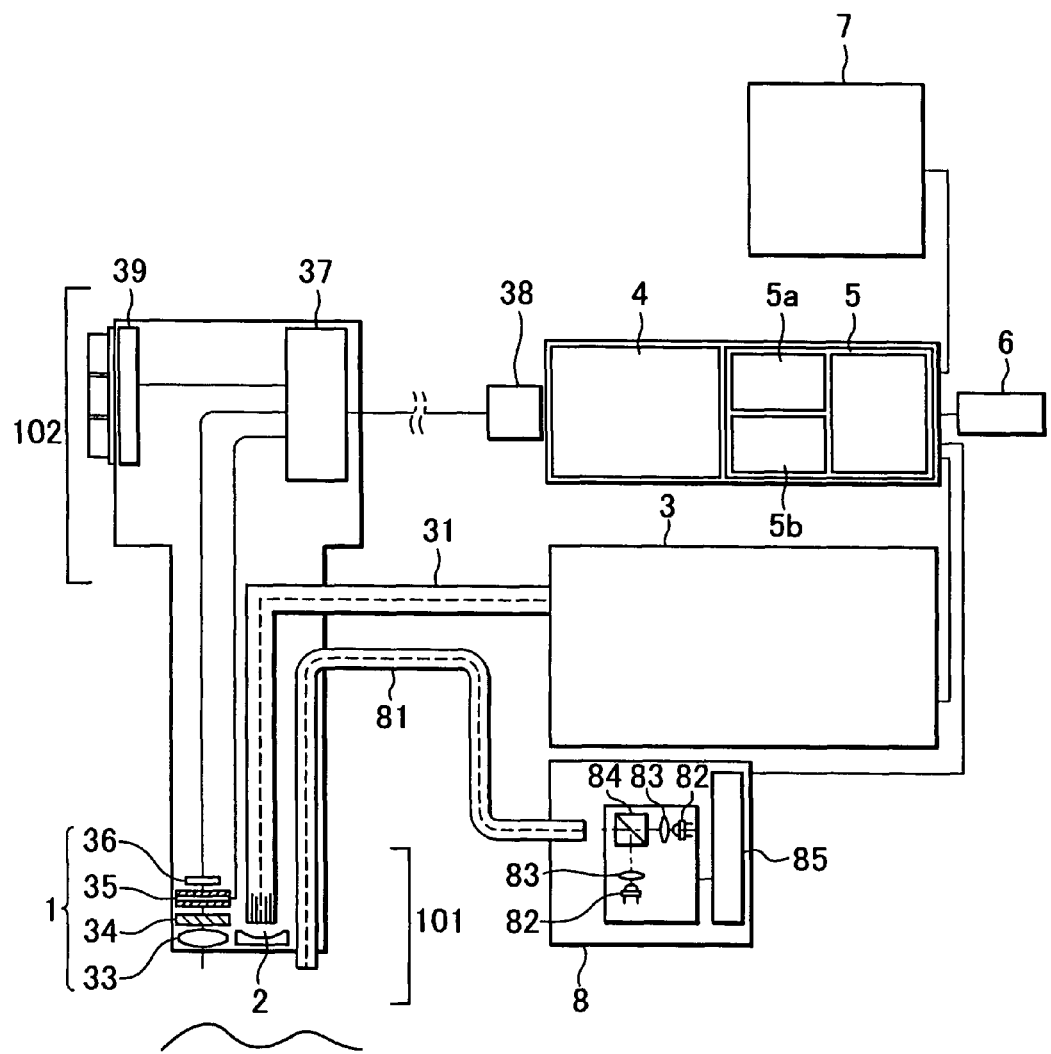
FIG. 12 shows the arrangement of various components of a fluorescent endoscope device according to Embodiment 1 of the present invention.

The construction of a fluorescent endoscope device according to Embodiment 1 of the invention will now be explained with reference to FIG. 12. Imaging unit 1 and illumination unit 2 are arranged at the insertion end 101 of the endoscope. The illumination unit 2 connects to the light source unit 3 by an optical transmission means, such as a light guide 31, and irradiates light supplied by the light source unit 3 onto the surface of living organism tissue via a lens having a diffusion effect. The light source unit 3 has a similar construction to that explained using FIG. 3, so further description thereof will be omitted. The imaging unit 1 is equipped with an objective optical system 33, an image pickup device 36, an excitation light cut-off filter 34, and a variable transmittance optical element that can be controlled so as to change the wavelength range of light that it transmits. The variable transmittance optical element may be located between the object-side surface of the objective optical system 33 and the image plane of the image pickup device 36.

The variable transmittance optical element may be, for example, an etalon or a liquid crystal tunable filter. The peak transmittance wavelength of an etalon may be changed, for example, by adjusting an air gap spacing between two highly reflective surfaces. The peak transmission wavelength of a liquid crystal tunable filter may be changed by electrically adjusting the crystal array of the liquid crystal tunable filter. As shown in FIG. 12, the imaging unit 1 of Embodiment 1 is equipped with an etalon 35 having a first wavelength transmission range for wavelengths less than 600 nm (see FIG. 8B) wherein, even if the air gap spacing is changed, the transmittance is 50% or greater, and a second wavelength transmission range for wavelengths of 600 nm or greater (see FIG. 8B) wherein, when the air gap spacing is increased, the wavelength region transmitted by the etalon changes to longer wavelengths. The etalon connects to a drive circuit 37 in the operating section 102 of the endoscope. The drive circuit 37 is connected to the control unit 4 via the connector 38, and receives synchronous signals from the control unit 4 that control the operation of the etalon. The drive circuit 37 also is connected to the image pickup device 36 and a switch 39 in the operating section 102, and transmits signals between the control unit 4 and the image pickup device 36 and/or the switch 39 in operating section 102.

The control unit 4 controls the timing of: (1) the light source unit 3 that creates an excitation light and supplies the excitation light to the illumination unit 2; (2) the imaging unit 1 that forms and acquires a fluorescent image using light emitted from the surface of the living organism tissue; and (3) the etalon 35 that changes the air gap spacing. The image signals acquired by the imaging unit 1 are processed by an image processing unit 5. The image processing unit 5 is equipped with a memory circuit 5a that temporarily stores image signal data, and a operating circuit 5b that performs operations required for image processing based on the data stored in the memory circuit 5a. Further, an external recording device 6, such as a DVD or HDD, connects to the image processing unit 5, and is designed so that image signal data acquired by the imaging unit 1 and image data processed by the image processing unit 5 can be recorded and saved. The image signal data recorded in the external recording device 6 is appropriately reproducible, and new image processing can be performed by taking the image signal data into the image processing unit 5. Fluorescent images processed by the image processing unit 5 are displayed on the TV monitor 7.

Further, the fluorescent endoscope device of the present embodiment is constructed so that excitation lights can be supplied to living organism tissue from another light source unit 8 that is equipped with multiple semiconductor elements that emit coherent lights having different wavelengths via a light guide 81. The light source unit 8 is equipped with semiconductor elements 82, 82, and optical systems 83, 83 that direct the coherent light emitted from the semiconductor elements 82, 82 onto the incident end face of the light guide 81. An optical element 84 (such as a beam splitter) is positioned between the semiconductor elements 82, 82 and the incident-end surface of the light guide 81 and functions to direct the light from the semiconductor elements 82, 82 into the light guide 81. A drive circuit 85 controls the energizing/de-energizing of the semiconductor elements 82, 82 so as to control their emission states. The drive circuit 85 is connected to the control unit 4, and receives synchronous signals that are transmitted from the control unit 4. The emission state of the semiconductor elements 82, 82 is switched by the synchronous signals transmitted from the control unit 4. Coherent light emitted from the semiconductor elements 82, 82 is irradiated onto living organism tissue by the light guide 81 being introduced into the insertion end of the endoscope via the treatment tool insertion channel of the endoscope. Furthermore, it is also possible to arrange an optical element to diffuse light on the emission end face of the light guide 81. Also, it is possible to control the duration of supplying excitation lights to the light guide 81 by periodically shielding the coherent light emitted from the semiconductor elements 82, 82 while the emission state of these elements is kept constant.

Figure 13:
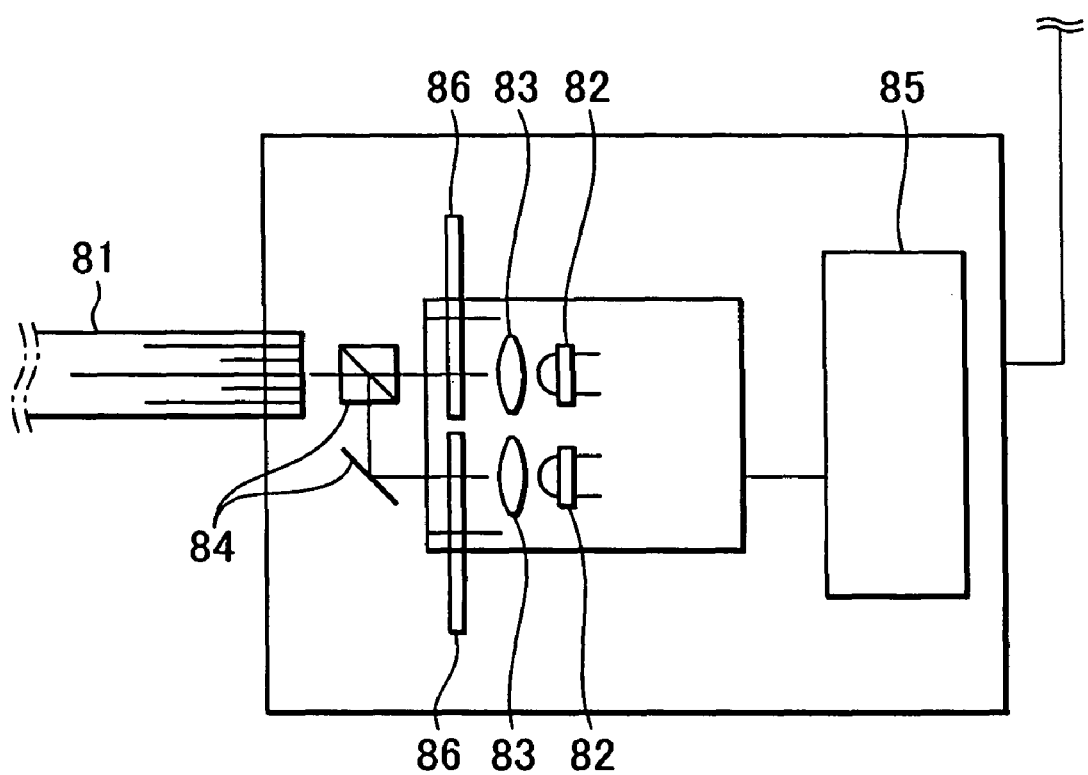
FIG. 13 shows an alternative construction for a light source unit to that of the light source unit 8 shown in FIG. 12.

As shown in FIG. 13, light choppers 86, 86 are arranged to periodically block light emitted by the semiconductor elements 82, 82. The light choppers 86, 86 are equipped with a sensor to detect a state in which the luminous flux has begun to be blocked and to detect a state when the luminous flux has begun to pass unimpeded, and these states are then transmitted to the control unit 4 via the drive circuit 85 and utilized to synchronize the timing for reading out image signals from the imaging unit 1 with the time periods that the light from the semiconductor elements is periodically blocked.

Figure 14A:
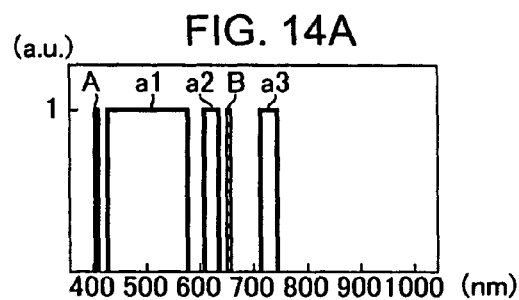
FIGS. 14A-14H are various diagrams used in describing basic operations of the fluorescent endoscope device according to Embodiment 1 of the present invention.
Figure 14B:
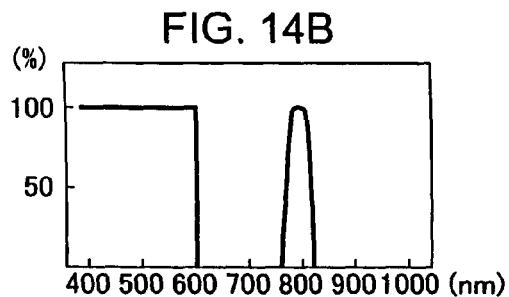
Figure 14E:
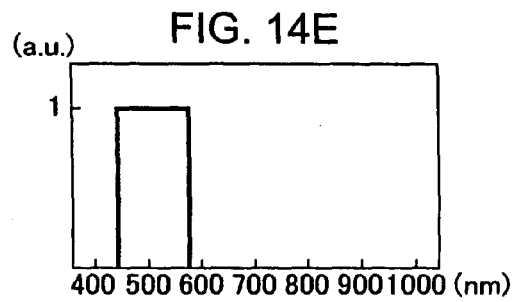
Figure 14C:
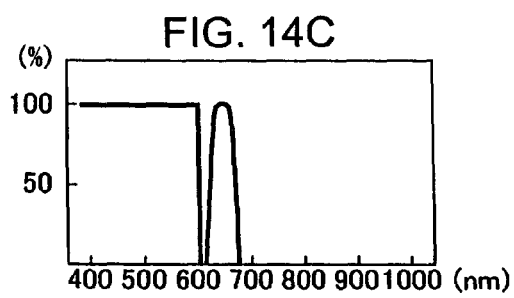
Figure 14F:
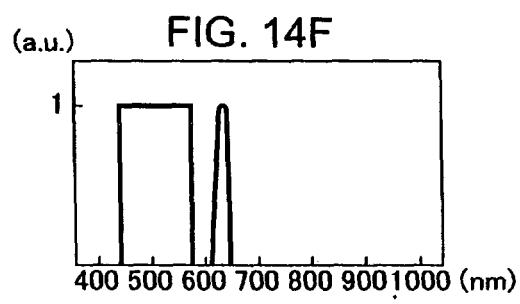
Figure 14D:
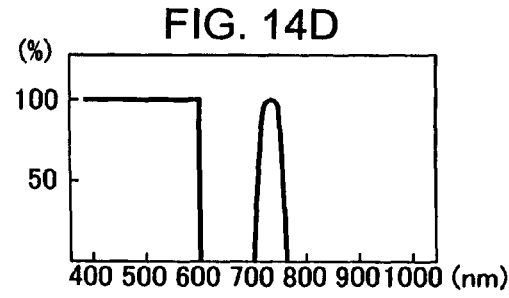
Figure 14G:
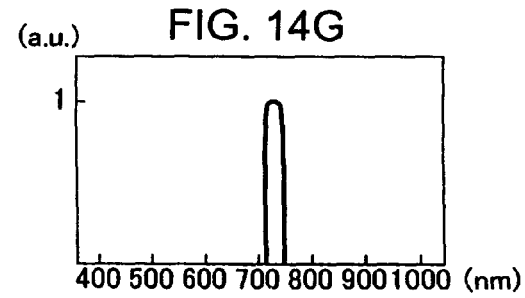
Figure 14H:
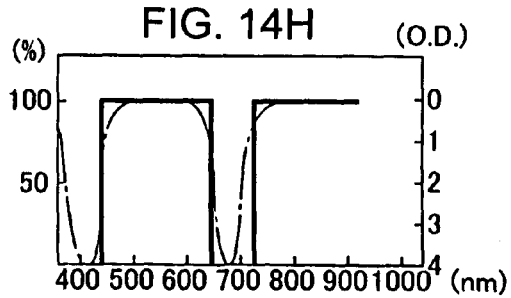

The basic operation of the fluorescent endoscope device of the present embodiment will now be described with reference to FIGS. 14A-14H. FIG. 14A is a conceptual illustration showing the excitation lights used and fluorescent lights that are detected by the fluorescent endoscope device. The vertical axis indicates the light intensity, in arbitrary units, of the excitation lights and of the fluorescent lights. The horizontal axis indicates the wavelength, in nm. FIGS. 14B, 14C and 14D show the spectral transmittance of the etalon in three different states. The vertical axis indicates the average % transmittance and the horizontal axis indicates the wavelength, in nm. FIGS. 14E, 14F and 14G show the intensity of light received by the image pickup device for the three different states corresponding to the timing of the irradiations onto the etalon and the etalon states shown in FIGS. 14B, 14C and 14D, respectively. Once again, the vertical axis indicates the light intensity, in arbitrary units, and the horizontal axis indicates the wavelength, in nm. FIG. 14H shows the spectral transmittance of the excitation light cut-off filter according to Embodiment 1. In FIG. 14H, the solid line indicates the ideal % transmittance property of the excitation light cut-off filter 14, for which the left-side vertical scale applies. On the other hand, the chain line indicates the best optical density property of the excitation light cut-off filter 14 which may be realized as an actual filter. The right-side vertical scale applies to the optical density property. That is, the ideal state is shown by the % transmittance. The actual state is shown by the optical density.

As shown in FIG. 14A, in the fluorescent endoscope device of this embodiment, two different excitation lights are irradiated onto a living tissue, and three types of fluorescent images having different peak wavelengths can be obtained. More specifically, coherent light in narrow-band wavelength region A having an intensity distribution with a peak intensity at 405 nm excites collagen or elastin and creates auto-fluorescence in the wavelength region a1. Simultaneously, it excites porphyrin and creates auto-fluorescence in the wavelength region a2. The wavelength region a1 is in the range of 420 nm-580 nm, and the wavelength region a2 is in the range of 610 nm-640 nm. Further, coherent light in narrow-band wavelength region B having an intensity distribution with a peak intensity at 660 nm excites the fluorescent probes (that have been previously administered from outside the body and have combined with lesion tissue) and creates fluorescence in the wavelength region a3. The wavelength region a3 is in the range of 710 nm-740 nm. The excitation light cut-off filter 34 is arranged in the imaging unit and is characterized by having a % transmission of 70% or greater in the 420 nm-640 nm wavelength range and in the 710 nm-740 nm wavelength range (see the left scale of FIG. 14H). As shown in FIG. 14H, the optical density (as measured using the right scale) is 4 or greater in the wavelength ranges of 400 nm-430 nm and 650 nm-670 nm, respectively, so that the excitation light cut-off filter 34 sufficiently shields the coherent light in narrow-band wavelength region A and the coherent light in narrow-band wavelength region B.

Figure 15:
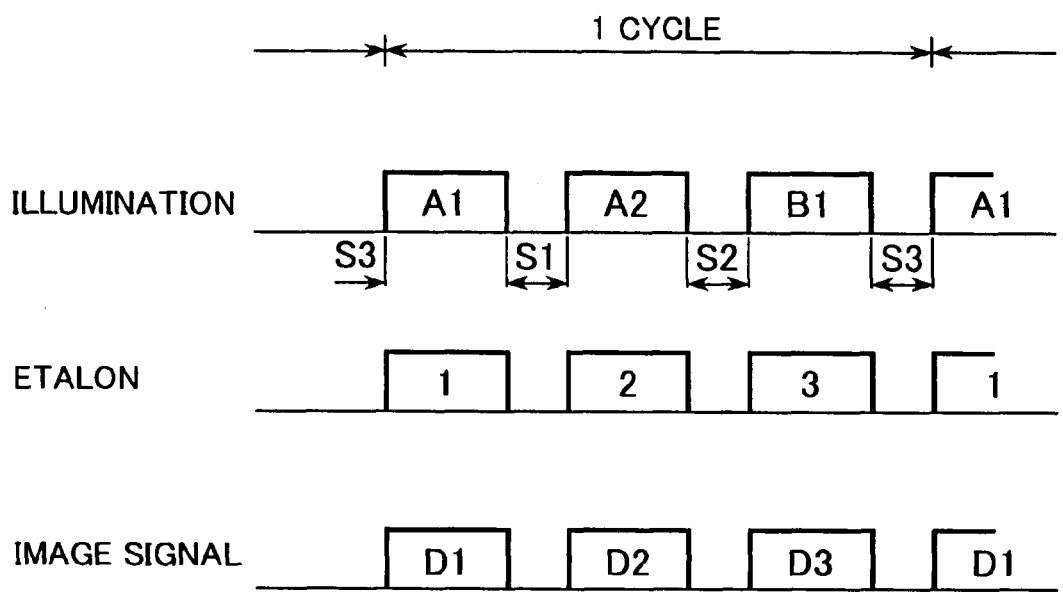
FIG. 15 is a timing chart showing the timing relationships during operation of the fluorescent endoscope device of Embodiment 1 for one cycle of the rotating disc 24, including the illumination periods, the etalon states, and the image signals acquired by the imaging unit.

FIG. 15 is a timing chart that shows the relationships of the illumination states, the etalon states, and the fluorescent image signals obtained by the imaging unit 1 for Embodiment 1, as will be discussed in detail later. Although there is no rotating disc used in this embodiment, one cycle in FIG. 15 corresponds to one cycle in FIG. 12, during which the rotating disc turns once around the rotating axis thereof.

If there is an instruction from an operator of the endoscope by the action of depressing the switch 39 to begin acquiring a fluorescent image, the control unit 4 transmits a synchronous signal to the light source unit 3, the imaging unit 1 and the drive circuit 37 of the etalon. The etalon may be set to at least three different transmission states by changing the air gap spacing using control signals from the drive circuit 37. In a period when the light source unit 8 produces coherent light in the narrow-band wavelength region A, the etalon is successively set to the following states:

state 1—a state wherein, of the fluorescent lights a1, a2, and a3 shown in FIG. 14A, only light in the wavelength region a1 is transmitted, as illustrated in FIG. 14B; and state 2—a state wherein, of the fluorescent lights a1, a2, and a3 shown in FIG. 14A, only light in the wavelength regions a1 and a2 is transmitted, as illustrated in FIG. 14C.

In state 1, the air gap spacing of the etalon is the longest of the three states. At this time, in the second wavelength transmission band of the etalon, the full width of the intensity profile as measured between the half-maximum intensity points is 60 nm or less and the peak transmission wavelength is on the long-wavelength side of 740 nm. In state 2, the air gap spacing of the etalon is the shortest of the three states. At this time, in the second wavelength transmission band of the etalon, the full width of the intensity profile as measured between the half-maximum intensity points is 60 nm or less and the transmission peak is in the wavelength range of 610-640 nm. When the etalon is set to be in state 1, only light in the wavelength region a1 is received by the image pickup device 36 (FIG. 14E). When the etalon is set to be in state 2, fluorescence in the wavelength regions a1 and a2 is received by the image pickup device 36 (FIG. 14F).

On the other hand, the etalon is set to the following state in a period when coherent light in the narrow-band wavelength region B is produced by the light source unit 8:

state 3—a state wherein, of the fluorescent lights a1, a2 and a3 shown in FIG. 14A, only light in the wavelength regions a1 and a3 is transmitted (FIG. 14D).

The air gap spacing of the etalon in state 3 is set to be bigger than in state 2 and smaller than in state 1. At this time, in the second wavelength transmission band of the etalon, the transmission peak is in the wavelength range of 710-740 nm, and the full width of the intensity profile as measured between the half-maximum intensity points is 60 nm or less. When the etalon is set to be in state 3, a fluorescence in the wavelength region a3 is received by the image pickup device 36 (FIG. 14G).

As shown by the timing chart of FIG. 15, during a first illumination period A1, coherent light in the narrow-band wavelength region A is emitted by the illumination unit 2 and the etalon is set to be in state 1. As a result, the imaging unit 1 acquires image signals D1 resulting from fluorescent components of the wavelength region a1. The image signals D1 are then read out during the next period S1 when the excitation light is shielded and are stored in a memory circuit 5a of the image processing unit 5. During a second illumination period A2 coherent light in the narrow-band wavelength region A is emitted by the illumination unit 2 and the etalon is set to be in state 2. As a result, the imaging unit 1 acquires image signals D2 comprising fluorescent components of the wavelength regions a1 and a2. The image signals D2 are then read out during the next period S2 when the excitation light is shielded and are stored in the memory circuit 5a of the image processing unit 5. During a third illumination period B1 coherent light in the narrow-band wavelength region B is emitted by the illumination unit 2 and the etalon is set to be in the state 3. As a result, the imaging unit 1 acquires image signals D3 comprising fluorescent components of the wavelength region a3 while the illumination light in the narrow-band wavelength region B is shielded from the image pickup device and the image signals D3 are stored in the memory circuit 5a of the image processing unit 5.

Figure 16A:
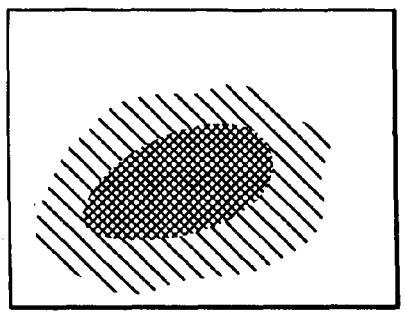
FIGS. 16A-16D are diagrams showing various typical fluorescent images that may be displayed on the screen of a TV monitor 7 using the fluorescent endoscope device according to Embodiment 1 of the present invention.
Figure 16B:
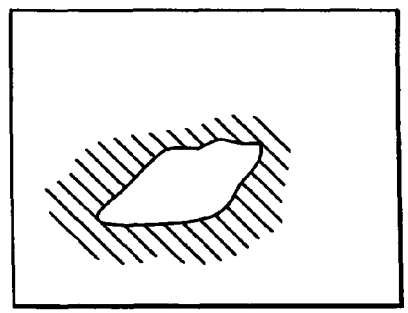
Figure 16C:
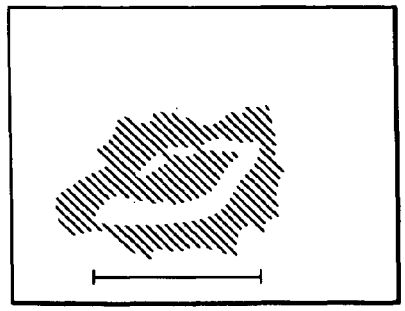
Figure 16D:
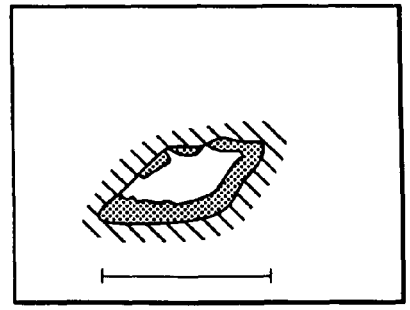

The two kinds of excitation lights (namely, coherent light in the narrow-band wavelength region A and coherent light in the narrow-band wavelength region B) are repeatedly irradiated onto a living body tissue surface, with the above three illumination states A1, A2 and B1 forming one cycle. FIG. 16A shows an auto-fluorescent image using light emitted by collagen and elastin that has been formed using the image signals D2, FIG. 16B shows an auto-fluorescent image using light emitted by porphyrin that has been formed using the image signals E1, FIG. 16C shows a fluorescent image from a fluorescent probe combined with lesion tissue that has been formed using the image signals D3, and FIG. 16D is a quasi-color-coded image that has been formed using all three image signals D2, E1, and D3. In the quasi-color-coded image, a normal site, a site wherein the surface layer of a normal tissue undergoes inflammation, and a lesion site may be distinguished using different colors. The image processing unit 5 can process these four images so that they can be displayed on a TV monitor 7 with the same image size and side-by-side, or it can process these four images by changing the display magnification for each image. Thus, a diagnosis can be performed that uses additional information that previously was not available, and this enables the accuracy of diagnosis to be further improved.

Figure 17:
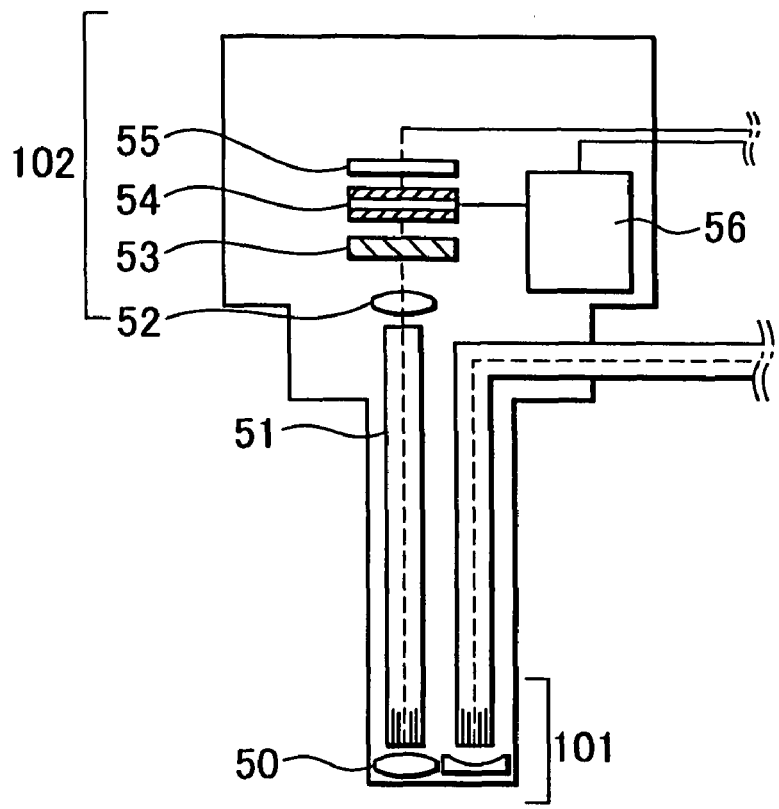
FIG. 17 is a diagram showing an alternative construction example for a fluorescent endoscope device according to Embodiment 1.

Although the imaging unit 1 used in the fluorescent endoscope device of Embodiment 1 is comprised of the objective optical system 33, the image pickup device 36, and the excitation light cut-off filter 34 and the etalon that are arranged between the object-side surface of the objective optical system 33, other designs are possible. For example, as shown in FIG. 17, an endoscope may be designed such that an object image is obtained by an objective optical system 50 that is arranged at the tip of the insertion part end 101. The object image can be transmitted to the operating section 102 by an optical image transmitting means, such as an optical cable 51, etc., so as to be acquired by an image pickup device 55 of an imaging optical system 52 that is arranged in the operating section 102 of the endoscope. An etalon 54 may be arranged between the image pickup device 55 and the imaging optical system 52, and an excitation light cut-off filter 53 may be arranged between the object-side surface of the objective optical system 50 and the etalon 54. Moreover, the transmission state of the etalon 54 can be controlled by a drive circuit 56 in the operating section 102 of the endoscope.

In such an endoscope, the tip of the insertion part end 101 can be made to have a small diameter; therefore it is suitable for observing biological tissues of the digestive tract, even of small animals such as mice, without injuring them.

Figure 18:
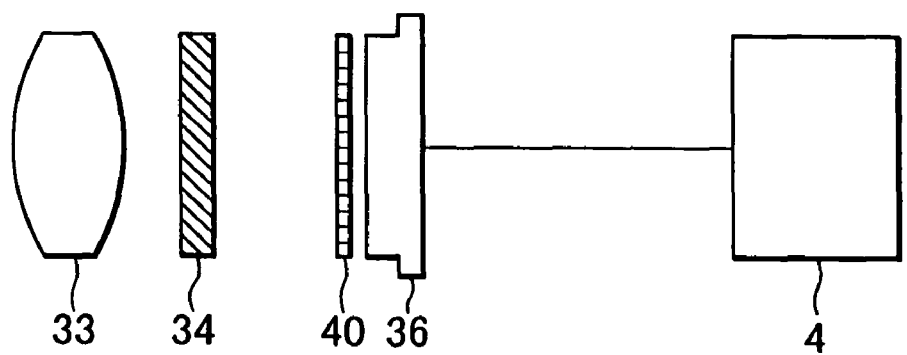
FIG. 18 is a diagram showing an alternative construction example of the imaging unit 1 used for the fluorescent endoscope device of Embodiment 1.
Figure 19:
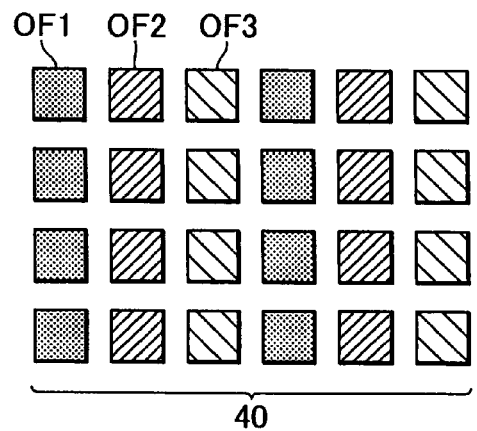
FIG. 19 is a diagram showing an arrangement of optical filters OF1, OF2, and OF3 that comprise an optical filter array 40.
Figure 20A:
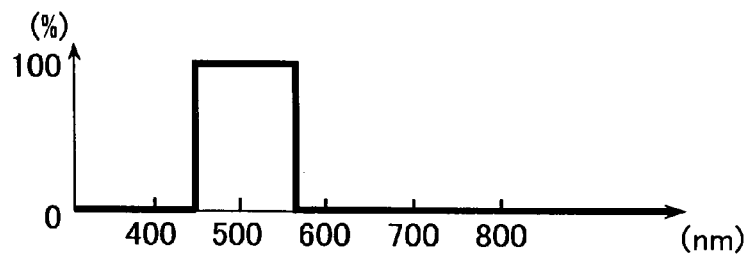
FIGS. 20A-20C show the % transmittance of the optical filters OF1, OF2 and OF3, respectively.
Figure 20B:
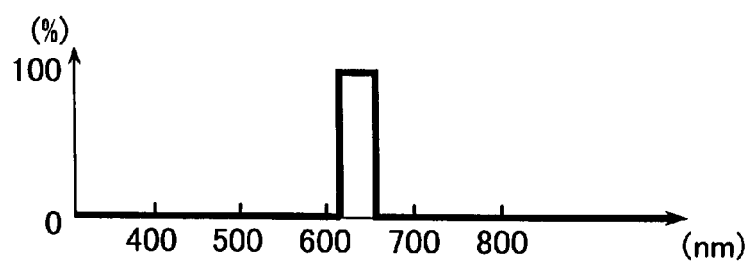
Figure 20C:
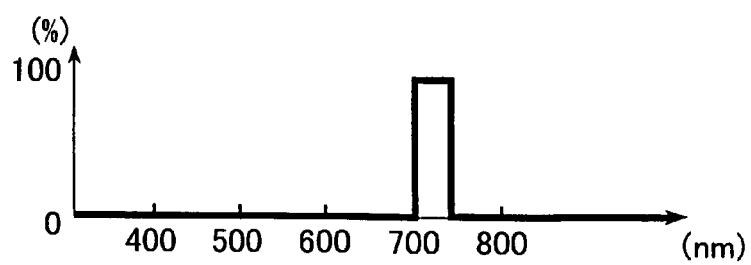

As shown in FIGS. 18-20C, the imaging unit 1 can be designed with an alternative construction to that illustrated for Embodiment 1. FIG. 18 is a diagram showing an alternative construction example of an imaging unit 1 used for the fluorescent endoscope device in Embodiment 1. FIG. 19 is a diagram showing an arrangement of optical filters OF1, OF2, and OF3, each of which are arranged in an array, on the optical filter 40, and FIGS. 20A-20C show the % transmittance of the optical filters OF1, OF2 and OF3, respectively. The optical filters OF1, OF2 and OF3 are arranged side-by-side in an array for transmitting lights of different wavelength bands so that individual optical filters of the array may be superimposed on different pixels of the image pickup device 36. Thus, the optical filter array may be used in lieu of an etalon so that multiple fluorescent images can be individually obtained.

The following three types of filters having different transmission characteristics are used for the optical filter 40:

(1) an optical filter OF1 having an average % transmittance of at least 50% throughout a wavelength range of 420 nm-580 nm, and an average % transmittance of 5% or less for other wavelengths in the range of 400 nm-800 nm (FIG. 20A);

(2) an optical filter OF2 having an average % transmittance of at least 50% throughout a wavelength range of 610 nm-640 nm, and an average % transmittance of 5% or less for other wavelengths in the range of 400 nm-800 nm (FIG. 20B); and (3) an optical filter OF3 having an average % transmittance of at least 50% throughout a wavelength range of 710 nm-740 nm, and an average % transmittance of 5% or less for other wavelengths in the range of 400 nm-800 nm (FIG. 20C).

In the example shown in FIG. 19, optical filters OF1, OF2, OF3 that are arranged in vertical columns are illustrated. Therefore, if fluorescence is detected for each pixel array on which the optical filters having the same transmission characteristics are superimposed, multiple fluorescent images can be individually obtained in different wavelength bands. In the case of using such an array of optical filters, a sequential reading of image pickup signals is possible, and a shielding period for reading the image signals in an illumination period is unnecessary. Therefore, bright images can be acquired even from a relatively weak fluorescent substance. Moreover, fluorescent images at different wavelength bands can be separated. This enables, for example, the coherent light in the narrow-band wavelength region A and the coherent light in the narrow-band wavelength region B to be irradiated simultaneously, and thus the construction of light source unit 8 can be simplified. Furthermore, multiple fluorescent images can be individually obtained; therefore computation processing in the image processing unit 5 is not necessary and can be omitted.

EMBODIMENT 2

Figure 21:
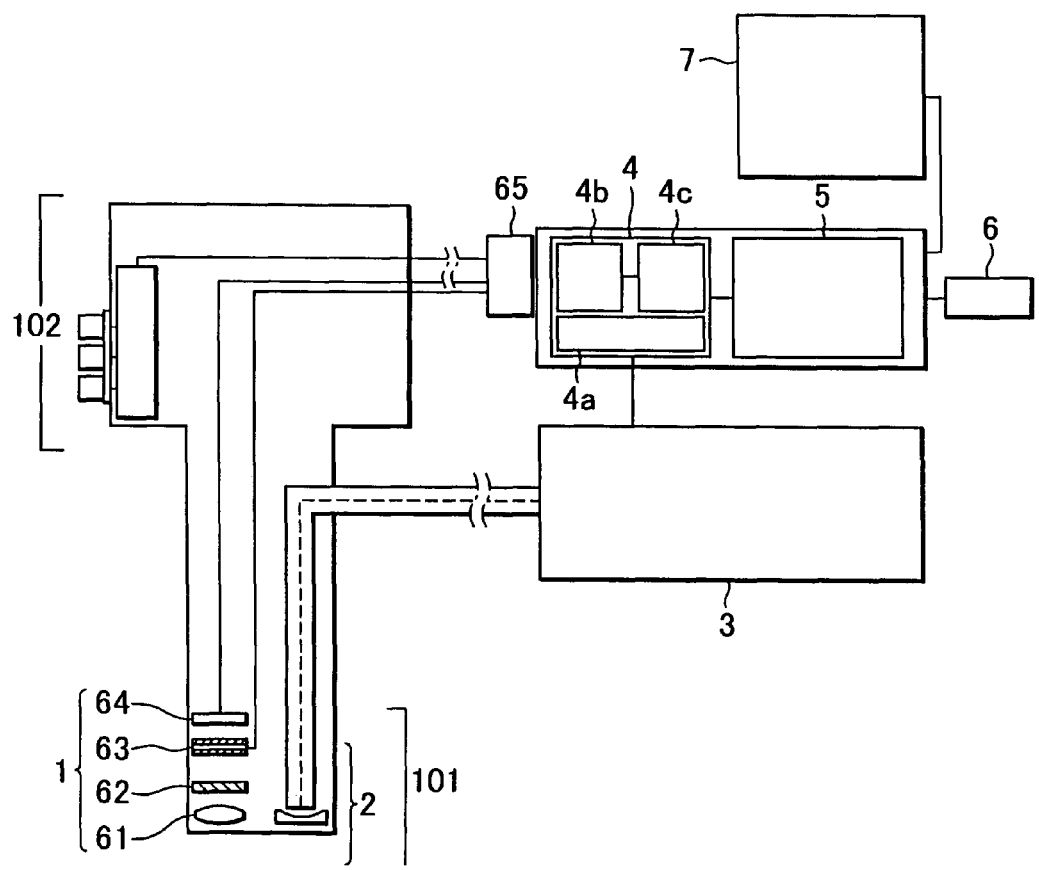
FIG. 21 shows the arrangement of various components of a fluorescent endoscope device according to Embodiment 2 of the present invention.

The basic construction of a fluorescent endoscope device according to Embodiment 2 of the invention is illustrated in FIG. 21 and will now be described. In a control unit 4 are provided: a timing control circuit 4a for controlling the timing of picking up a fluorescent image from the surface of biological tissue by an imaging unit 1 and for controlling the timing of changing the air gap spacing of an etalon 63 of the imaging unit 1 based on the timing of producing an excitation light and supplying it to an illumination unit 2 by a light source unit 3; a drive control circuit 4b for controlling the air gap spacing of the etalon 63; and a memory circuit 4c that holds recorded information necessary for changing the air gap spacing of the etalon. A memory chip that stores information, such as a production series number of the imaging unit 1, the type of the etalon, etc., is provided in a connector 65 for connecting the endoscope and the control unit 4. When the connector 65 is connected to the control unit 4, the stored information of the memory chip is read from the memory chip in the connector 65 and sent to the control unit 4. The drive control circuit 4b of the control unit 4 automatically sets up an operating environment of the etalon 63 most suited for connecting the imaging unit 1 by using the read-in information concerning the imaging unit 1 and the information necessary for operational control of the etalon that is stored in the memory circuit 4c. Image signals obtained by the imaging unit 1 are processed by an image processing unit 5 and then are displayed on a TV monitor 7. The construction of the image processing unit 5, a recorder 6 and TV monitor 7 are the same as in Embodiment 1 and will not be further discussed.

Figure 22A:
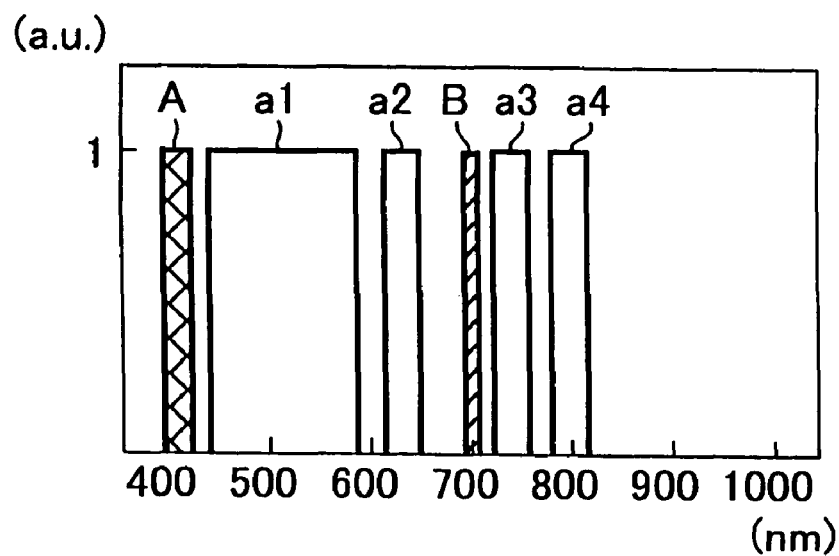
FIGS. 22A-22J are various diagrams used in describing the basic operation of a fluorescent endoscope device according to Embodiment 2.

Basic operations of the fluorescent endoscope device according to Embodiment 2 will now be described with reference to FIGS. 22A-22J and FIG. 23. FIG. 22A is a conceptual illustration that shows the relationship between the wavelength ranges of excitation lights generated by the light source unit 3 and the wavelength ranges of the fluorescence detected by the imaging unit 1. The vertical axis indicates the light intensity of the excitation lights and of the fluorescence, in arbitrary units, and the horizontal axis indicates the wavelength, in nm. FIGS. 22B-22E show the % transmittance versus incident light wavelength of the etalon 63 in four different states.

In FIGS. 22B-22E the solid lines indicate the ideal % transmittance property of the etalon 63, for which the left-side vertical scale applies. On the other hand, the chain line indicates the best optical density property of the etalon 63 which may be realized as an actual etalon, for which the right-side vertical scale applies. That is, the ideal state is shown by the % transmittance. The actual state is shown by the optical density. The horizontal axis is the wavelength, in nm.

Figure 22J:
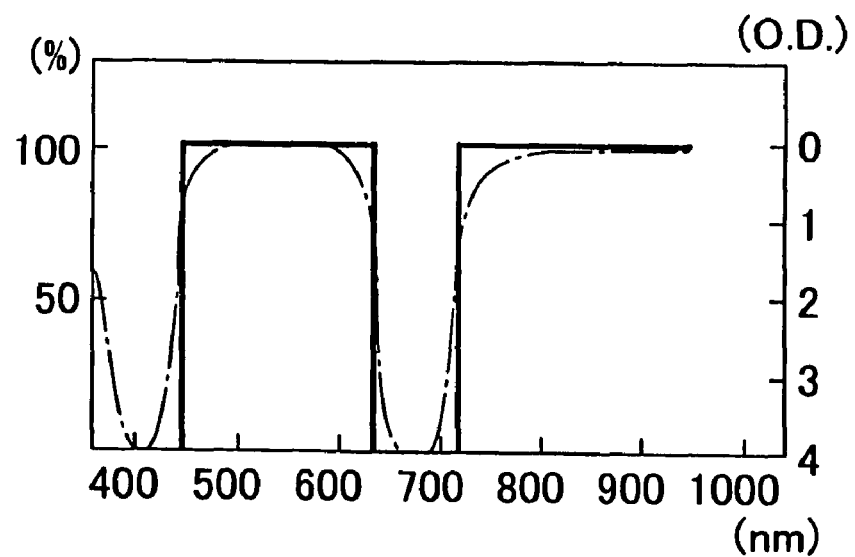

FIGS. 22F-22I show the intensity of light received by an image pickup device 64 that acquires an image due to the light transmitted by the etalon 63 when the etalon has the transmission characteristic shown in the graph to the left of each figure. Thus, FIGS. 22F, 22G, 22H, and 22I show the intensity of light received by the image pickup device 64 that acquires an image corresponding to the timing of the irradiations onto the etalon 63 for the etalon states having transmission characteristics as shown in FIGS. 22B, 22C, 22D, and 22E, respectively. The vertical axis indicates the light intensity, in arbitrary units, and the horizontal axis indicates the wavelength, in nm. FIG. 22J is a graph showing the transmission characteristics of an excitation light cut-off filter 62 for an incident ray that is parallel to a normal to the surface of the cut-off filter 62. In FIG. 22J the solid line indicates the ideal % transmittance property of the excitation light cut-off filter 62, for which the left-side vertical scale applies. On the other hand, the chain line indicates the best optical density property of the excitation light cut-off filter 62 which may be realized as an actual filter, with optical density being defined as per Equation (A) above. The right-side vertical scale applies to the optical density property. That is, the ideal state is shown by the % transmittance. The actual state is shown by the optical density. The horizontal axis is the wavelength, in nm.

As shown in FIG. 22A, in the fluorescent endoscope device of this embodiment, two different excitation lights are irradiated onto a biological tissue and four kinds of fluorescent images having different peak wavelengths can be obtained. An excitation light in the narrow-band wavelength region A (400 nm-430 nm) excites collagen and elastin to generate an auto-fluorescence in a wavelength region a1 and simultaneously excites porphyrin to generate an auto-fluorescence in a wavelength region a2. The wavelength region a1 is 440 nm-580 nm, and the wavelength region a2 is 610 nm-640 nm. An excitation light in the narrow-band wavelength region B (680 nm-700 nm) excites a fluorescent probe that has combined with a substance k1 that originates in a lesion tissue so as to generate a fluorescence in a wavelength region a3 and simultaneously excites a fluorescent probe that has combined with a substance k2 that originates in a lesion tissue so as to generate a fluorescence in a wavelength region a4. The wavelength region a3 is 710 nm-740 nm, and the wavelength region a4 is 770 nm-800 nm. An excitation light cut-off filter 62 is arranged in the imaging unit 1 and has a % transmittance in the wavelength ranges of 440 nm-640 nm and 710 nm-800 nm of over 70%, and an optical density over the entirety of the narrow-band wavelength regions A and B that exceeds 4 (FIG. 22J). Thus, the excitation lights in the narrow-band wavelength regions A and B (i.e., in the wavelength ranges of 400 nm-430 nm and 680 nm-700 nm, respectively) are fully shielded by the excitation light cut-off filter 62.

If an instruction for starting the acquirement of a fluorescent image is sent from an operator of the endoscope to the fluorescent endoscope device, the control unit 4 transmits a signal for switching the light source unit 3 to an excitation light production mode. If the light source unit 3 receives this signal, the rotary shaft of rotary disc 24 moves to a predetermined position and rotates (after a short period) at a fixed speed.

Figure 23:
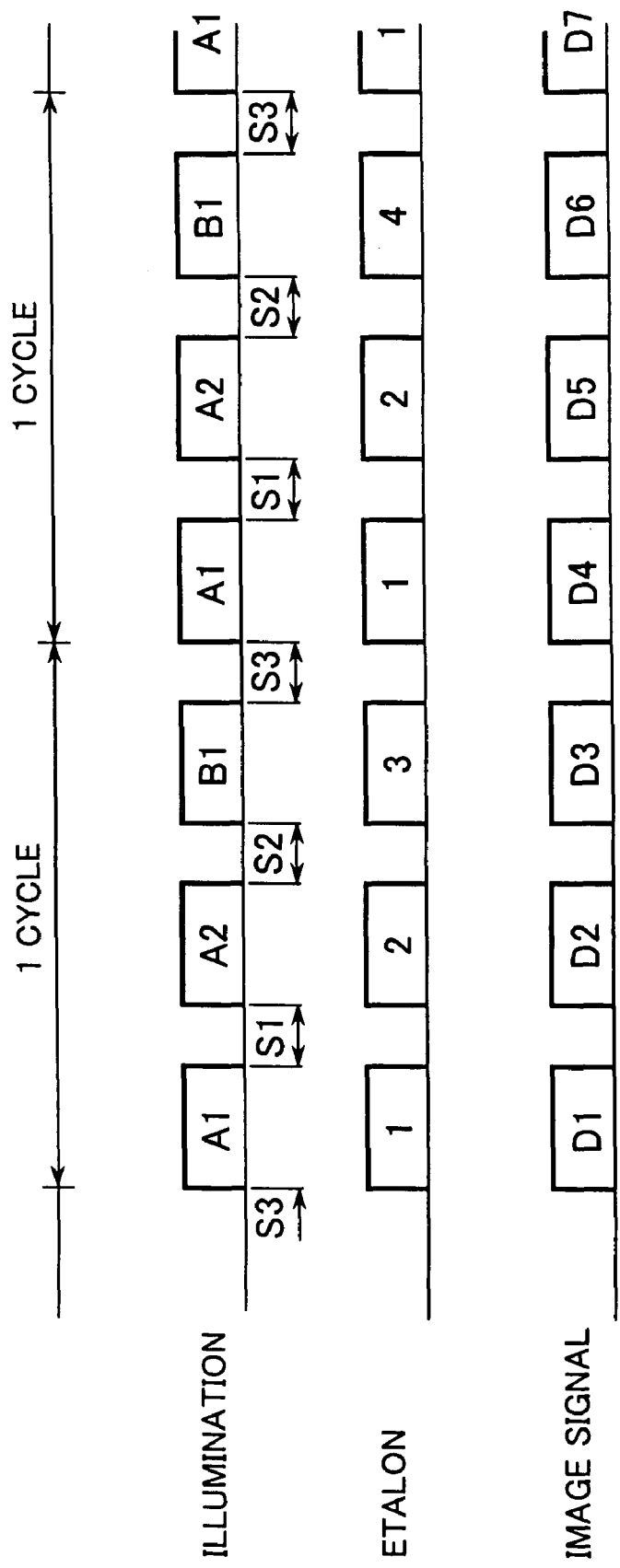
FIG. 23 is a timing chart showing the timing relationships during operation of the fluorescent endoscope device of Embodiment 2 for two cycles of the rotating disc 24, including the illumination periods, the etalon states, and the image signals acquired by the imaging unit.

FIG. 23 is a timing chart showing the timing among the illumination periods, the states of the etalon, and fluorescent image signals obtained by the image pickup device over two cycles of illumination by the rotary disc 24, as will be discussed in detail later.

Figure 22B:
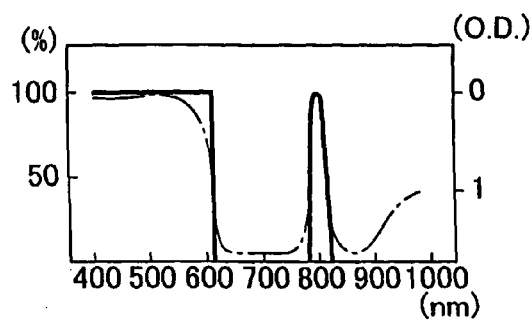
Figure 22F:
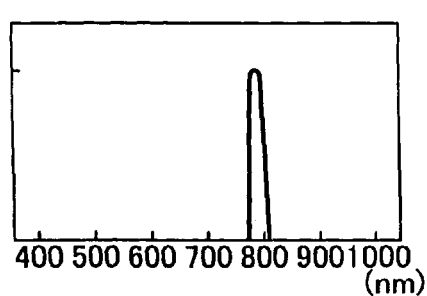
Figure 22C:
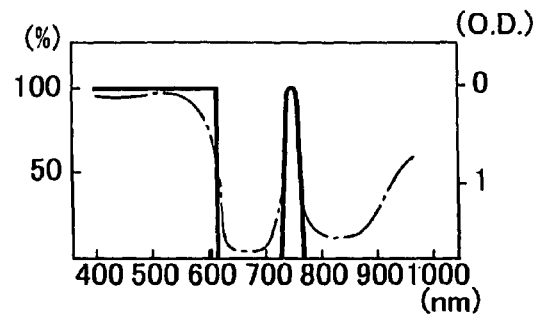
Figure 22G:
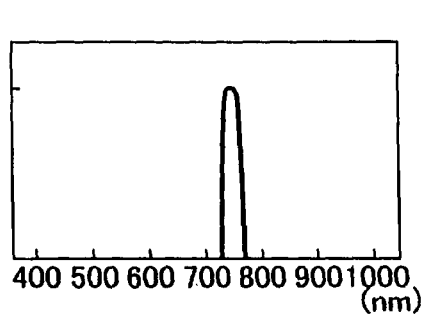
Figure 22D:
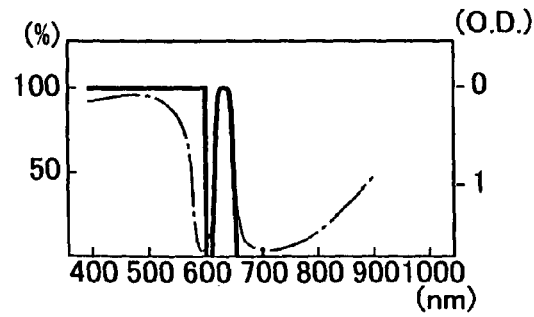
Figure 22H:
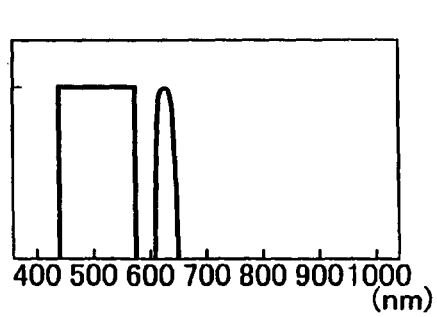
Figure 22E:
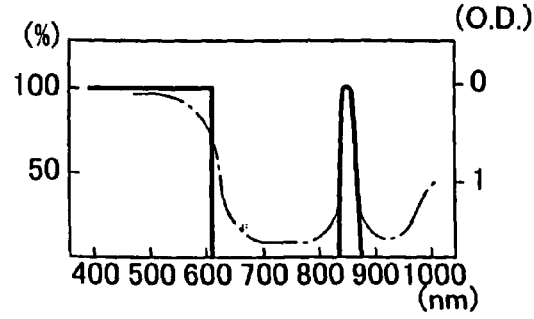
Figure 24:
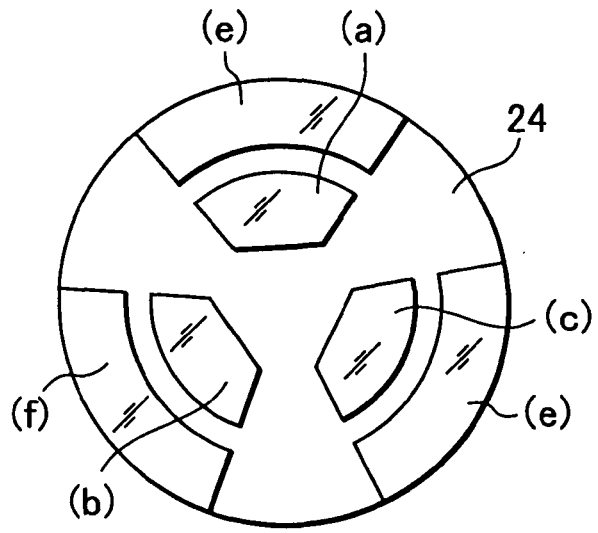
FIG. 24 illustrates various optical filters (a), (b), (c), (e), (e) and (f) that may be arranged in various windows of the rotating disc 24.

FIG. 24 is an axial view that shows the arrangement of optical filters (a), (b), (c), (e), (e), and (f) in the rotary disc 24. The optical filters (e), (e) and (f) for observing fluorescent images are repeatedly inserted into a light beam. The optical filters (e), (e) have a % transmittance that is greater than 50% throughout the wavelength range of 400 nm-430 nm, and the optical filter (f) has a % transmittance that is greater than 50% throughout the wavelength range of 680 nm-700 nm. As a result, three illumination periods, i.e., the first illumination period A1 and the second illumination period A2 in which the illumination unit irradiates excitation light in the narrow-band wavelength region A (400 nm-430 nm), and the third illumination period B1 in which the illumination unit irradiates excitation light in the narrow-band wavelength region B (680 nm-700 nm) are repeatedly irradiated for short periods due to there being shielding periods S1, S2, S3, respectively, between the three illumination periods in each cycle of the rotating disc 24. A sensor unit 25 (see FIG. 3) for detecting the moment when one optical filter finishes traversing the light beam and the moment that the next optical filter starts to traverse the light beam is provided in the light source unit 3. Signals detected by the sensor unit 25 are sent to the control unit 4 and used for synchronizing the timing for reading image signals from the imaging unit 1 and a timing for changing the air gap spacing of the etalon 63 with a period in which the illumination light is shielded. In this embodiment, the etalon 63 can be set to at least four different states by changing the air gap spacing using control signals from the drive circuit 4b. During one period of producing the excitation light in the narrow-band wavelength region A by the light source unit 3, the etalon 63 is successively set to the following two states:

state 1—a state wherein light in the wavelength region a1, but substantially no light in the wavelength region a2, is transmitted (FIG. 22E);

state 2—a state wherein light in wavelength regions a1 and a2 is transmitted (FIG. 22D).

Figure 22I:
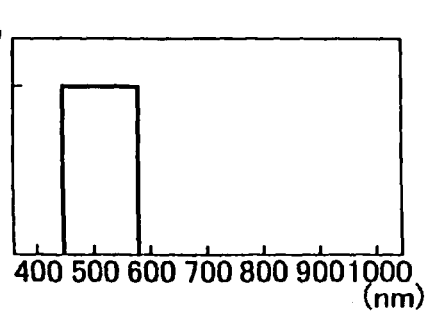

In state 1, the air gap spacing of the etalon 63 is set to be the longest of the four states. At that time, in the second wavelength transmission band of the etalon 63, the full width of the intensity profile as measured between the half-maximum intensity points is 30 nm or less and the wavelength transmission peak of the etalon is on the long-wavelength side of 800 nm. In state 2, the air gap spacing of the etalon 63 is set so as to be the shortest of the four different states. At that time, in the second wavelength transmission band of the etalon 63, the full width of the intensity profile as measured between the half-maximum intensity points is 30 nm or less and the transmission peak is in the wavelength range of 610 nm-640 nm. When the etalon 63 is set to be in state 1, only a fluorescence of wavelength region a1 is received by the image pickup device 64 (FIG. 22I). When the etalon 63 is set so as to be in state 2, fluorescence in the wavelength regions a1 and a2 is received by the image pickup device 64 (FIG. 22H).

On the other hand, in a period of producing excitation light in the narrow-band wavelength region B by the light source unit 3, the etalon 63 is set to the following two states:

state 3—a state wherein light in the wavelength regions a1 and a3 is transmitted (FIG. 22C);

state 4—a state wherein light in the wavelength regions a1 and a4 is transmitted (FIG. 22B).

In state 3 and state 4, the air gap spacings of the etalon 63 are set to be greater than in state 2 and smaller than in state 1.

However, the air gap spacing of the etalon in state 3 is smaller than the air gap spacing of the etalon in state 4. When the etalon 63 is set to state 3, in the second wavelength transmission band of the etalon 63, the full width of the intensity profile as measured between the half-maximum intensity points is 30 nm or less and the transmission peak is in a wavelength range of 710 nm-740 nm. At this time, a fluorescence of wavelength region a3 is received by the image pickup device 64 (FIG. 22G). When the etalon 63 is set to state 4, in the second wavelength transmission band of the etalon 63 the full width of the intensity profile as measured between the half-maximum intensity points is 30 nm or less and the transmission peak is in a wavelength range of 770 nm-800 nm. At this time, a fluorescence of wavelength region a4 is received by the image pickup device 64 (FIG. 22F).

As shown in the timing chart of FIG. 23, if one cycle is taken as from the commencement of the first illumination period A1 (in which the illumination unit 2 irradiates excitation light in the narrow-band wavelength region A) to the end of the third illumination period B1 in which the illumination unit 2 irradiates excitation light in the narrow-band wavelength region B, image data necessary for image processing for the fluorescent endoscope device of this embodiment must be obtained over two consecutive cycles. In a first cycle during a first illumination period A1, the illumination unit 2 irradiates excitation light in the narrow-band wavelength region A. With the etalon 63 set so as to be in state 1, the imaging unit 1 acquires image signals D1 composed of fluorescent light in the wavelength region a1. The image signals D1 are then read out during the next period S1 in which the excitation light is shielded and are stored in the memory circuit 5a of the image processing unit 5. The etalon 63 is then adjusted so as to be in state 2. During a second illumination period A2, the illumination unit 2 irradiates excitation light in the narrow-band wavelength region A. As a result, the imaging unit 1 acquires image signals D2 comprising fluorescent components of the wavelength regions a1 and a2. The image signals D2 are then read out during the next period S2 in which the excitation light is shielded and are stored in the memory circuit 5a of the image processing unit 5. During a third illumination period B1, the illuminating unit 2 irradiates excitation light in the narrow-band wavelength region B and the etalon 63 is adjusted so as to be in state 3. As a result, the imaging unit 1 acquires image signals D3 of fluorescent light in the wavelength region a3 while the etalon 63 is in state 3. The image signals D3 are then read out during the next period S3 in which the excitation light is shielded and are stored in the memory circuit 5a of the image processing unit 5.

In the next cycle, the etalon 63 is set to state 1 in the first illumination period A1 during which the illumination unit 2 irradiates excitation light in the narrow-band wavelength region A once again. As a result, the imaging unit 1 acquires image signals D4 of fluorescent light in the wavelength region a1. The image signals D4 are then read out during the next period S1 in which the excitation light is shielded and are stored in the memory circuit 5a of the image processing unit 5. The etalon 63 is then set to be in state 2 in the second illumination period A2 during which the illumination unit 2 irradiates excitation light in the narrow-band wavelength region A. As a result, the imaging unit 1 acquires image signals D5 comprising fluorescent components of the wavelength regions a1 and a2. The image signals D5 are then read out during the next period S2 in which the excitation light is shielded and are stored in the memory circuit 5a of the image processing unit 5. The etalon 63 is then set to be in state 4 in the illumination period B1 in which the illumination unit 2 irradiates excitation light in the narrow-band wavelength region B. As a result, the imaging unit 1 acquires image signals D6 comprising fluorescent components of the wavelength region a4. The image signals D6 are then read out during the next period S3 in which the excitation light is shielded and are stored in the memory circuit 5a of the image processing unit 5.

Image processing is performed based on image signals acquired during the above-discussed two cycles, which are repeated. The procedure of image processing by the image processing unit 5 is the same as previously discussed and therefore, further discussion will be omitted.

Figure 25A:
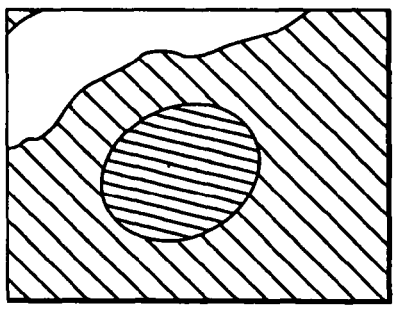
FIGS. 25A-25C are diagrams of typical types of fluorescent images that may be displayed on a TV monitor 7 using the fluorescent endoscope device of Embodiment 2.
Figure 25B:
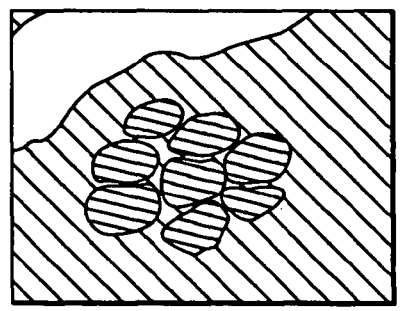
Figure 25C:
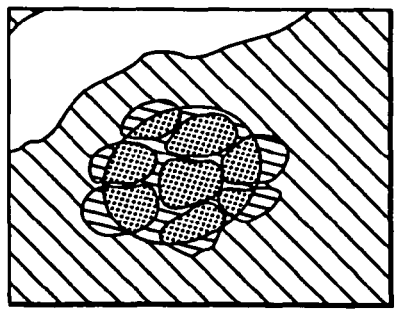

FIGS. 25A-25C are schematic diagrams that illustrate the kinds of fluorescent images that can be displayed on the TV monitor 7 using the fluorescent endoscope device of Embodiment 2. FIG. 25A is a quasi-color-coded image prepared based on the three kinds of image signals acquired in the above-mentioned first cycle. In the quasi-color-coded image, a normal site, a site where the surface layer of a normal tissue undergoes an inflammation, and a pathological site are displayed in separate, different colors. FIG. 25B is a quasi-color-coded image that has been prepared based on the three kinds of image signals acquired in the above-mentioned second cycle. FIG. 25C is a composite display of the image shown in FIG. 25A superimposed over the image shown in FIG. 25B, wherein the overlapped areas of the lesion site in FIG. 25A and FIG. 25B are emphatically displayed. For example, FIG. 25A may be an image which includes information relating to a substance k1 that originates in pathologically changing tissue, and FIG. 25B may be an image which includes information relating to a separate substance k2 that originates in pathologically changing tissue. Therefore, as shown in FIG. 25C, an image can be provided by synthesizing the information in FIGS. 25A and 25B so as to create a display in which the amount of information relating to the pathologically changing tissue is increased (as in FIG. 25C) and which therefore has a higher degree of reliability in terms of specifying a pathologically changing tissue.

In this manner, by using multiple fluorescent probes that selectively attach to and combine with different target substances that originate in pathologically changing tissue (for example, substances involved when there is malignancy in the pathologically changing tissue, or where the substance is involved at a time when the pathologically changing tissue is actively propagating) and by synthesizing a composite image from the various probes, the precision of diagnosis of pathologically changing tissue can be greatly enhanced, thereby enabling a high degree of precision in a diagnosis even though there may be only a small amount of histological change in terms of the composition of the living tissue, as occurs in the early stages of cancer and the like.

In the present embodiment (as in the embodiment shown in FIGS. 19-20C), in lieu of using an etalon, multiple optical filters may be positioned in an array immediately prior to the image-receiving surface of the image pickup device. If the multiple optical filters transmit light having respective, different peak wavelengths, multiple fluorescent images can be acquired simultaneously.

For example, four types of optical filters of different peak transmittances may be used, as follows:

(1) an optical filter (OF1) in which the % transmittance is 50% or greater for a wavelength range of 420 nm-580 nm, and the % transmittance is 5% or less for other wavelengths in the range of 400 nm-800 nm;

(2) an optical filter (OF2) in which the % transmittance is 50% or greater for a wavelength range of 610 nm-640 nm, and the average % transmittance is 5% or less for other wavelengths in the range of 400 nm-800 nm;

(3) an optical filter (OF3) in which the % transmittance is 50% or greater for a wavelength range of 710 nm-740 nm, and the average % transmittance is 5% or less for other wavelengths in the range of 400 nm-800 nm; and (4) an optical filter (OF4) in which the % transmittance is 50% or greater for a wavelength range of 770 nm-800 nm, and the average % transmittance is 5% or less for other wavelengths in the range of 400 nm-800 nm.

In this embodiment, four kinds of optical filters OF1, OF2, OF3 and OF4 are arranged on every four vertical pixel arrays of the image pickup device 64 and fluorescence is detected for each pixel array on which the optical filters having the same transmission characteristics are superimposed. Therefore, multiple fluorescent images can be individually acquired. With such a composition, it is possible to successively read out image signals, and there is no need to provide light shielding periods in order to read out image signals. This enables the illumination period to be made relatively long and thereby enables high quality image signals to be obtained even when the fluorescent lights are weak. In addition, since the fluorescent lights having different peak wavelengths can be separated, the excitation light in the narrow-band wavelength region A and the excitation light in the narrow-band wavelength region B can be simultaneously illuminated, making it possible to simplify the structure of the light source units. In addition, since multiple fluorescent images can be individually acquired, computation processing can be eliminated from the image processing unit 5.

EMBODIMENT 3

Figure 26A:
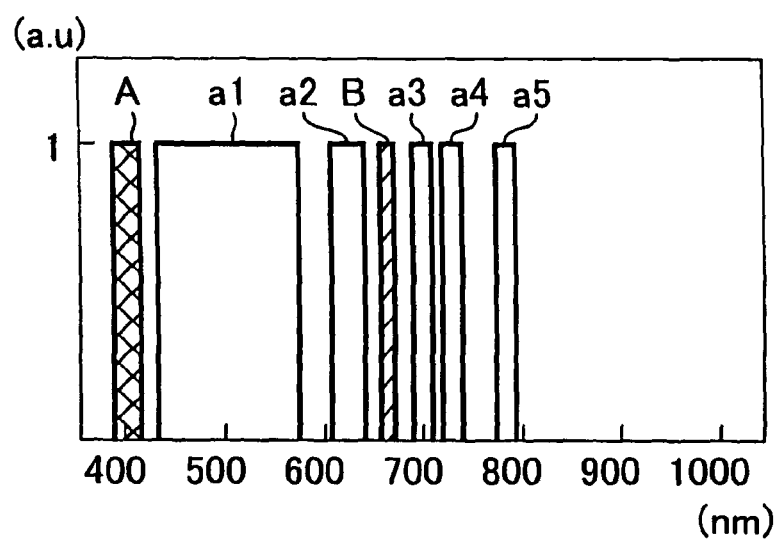
FIGS. 26A-26L are various diagrams used in describing the basic operation of a fluorescent endoscope device according to Embodiment 3.

The imaging unit 1, illumination unit 2 and light source unit 3 of Embodiment 3 are the same as in Embodiment 2 except for wavelength ranges of the excitation lights and of the fluorescent lights that are imaged and detected. Since the composition of the fluorescent endoscope device of the Embodiment 3 is generally the same as that of Embodiment 2, further construction details will be omitted. Rather, the basic operation of the fluorescent endoscope device of Embodiment 3, which differs from that of Embodiment 2, will be discussed with reference to FIGS. 26A-26L and FIG. 27. FIG. 26A is a conceptual illustration that shows the relationship between the wavelength ranges of excitation lights generated by the light source unit 3 and the wavelength ranges of fluorescence detected by the imaging unit 1 according to Embodiment 3. On the vertical axis are displayed the light intensities of the excitation lights and of the fluorescent lights, in arbitrary units. The horizontal axis shows the wavelength, in nm. FIGS. 26B-26F show the % transmittance of the etalon 63 on the vertical axis and the wavelength, in nm, on the horizontal axis for various states (i.e., caused by different air gap spacings) of the etalon which results in the etalon having different peak transmittances. FIGS. 26G-26K show the intensities of fluorescent light received by the image pickup device 64 after being transmitted by the etalon. The vertical axis indicates the intensity of the light, in arbitrary units, and the horizontal axis indicates the wavelength, in nm.

Figure 26L:
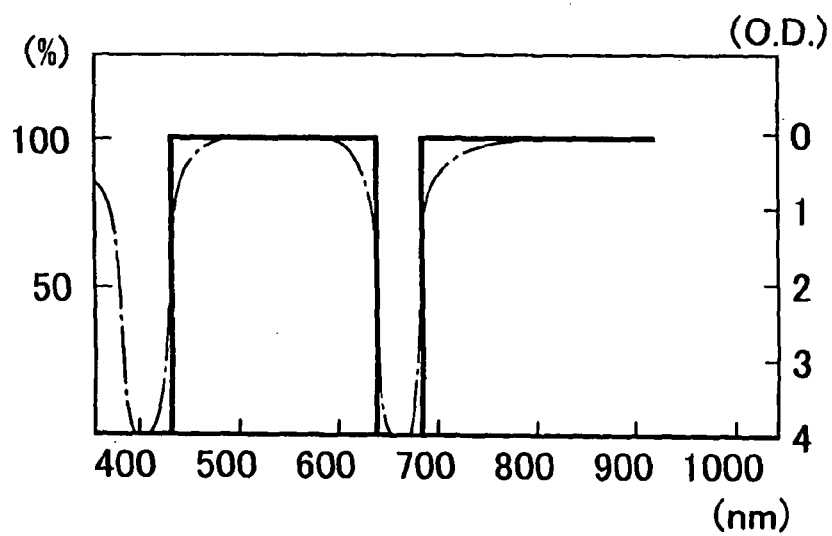

FIG. 26L shows optical characteristics of an excitation light cut-off filter 62 that may be arranged in the imaging unit 1. In FIG. 26L, the solid line indicates the ideal % transmittance of the excitation light cut-off filter 62 for a ray that is incident parallel to the surface normal of the cut-off filter, for which the left-side vertical scale applies. On the other hand, the chain line indicates the best optical density property of the excitation light cut-off filter which may be realized as an actual excitation light cut-off filter 62 for a ray that is incident parallel to the surface normal of the cut-off filter. The right-side vertical scale applies to the optical density, which is defined as per Equation (A) above. That is, the ideal state is shown by the % transmittance. The actual state is shown by the optical density.

As shown in FIG. 26A, with the fluorescent endoscope device of the present embodiment, five types of fluorescent images of respective different peak wavelengths can be acquired by illuminating living tissue using two different excitation lights. Excitation light in the narrow-band wavelength region A (400 nm-430 nm) is used that generates auto-fluorescent light in the wavelength region a2 (610 nm-640 nm) by exciting porphyrin, and it simultaneously also generates auto-fluorescent light in the wavelength region a1 (440 nm-580 nm) by exciting collagen and elastin. In addition, excitation light in the narrow-band wavelength region B (650 nm-670 nm) is used that generates: (1) fluorescent light in the wavelength region a3 (690 nm-710 nm) by exciting a fluorescent probe that has combined with a first substance k1 that originates in pathologically changing tissue; (2) fluorescent light in the wavelength region a4 (720 nm-740 nm) by exciting a fluorescent probe that has combined with a second substance k2 that originates in pathologically changing tissue; and (3) fluorescent light in the wavelength region a5 (770 nm-790 nm) by exciting a fluorescent probe that has combined with a third substance k3 that originates in pathologically changing tissue. The transmission characteristics of the excitation light cut-off filter that is arranged in the imaging unit 1 are such that the average % transmittance is 70% or greater in the wavelength ranges of 440 nm-640 nm and 690 nm-790 nm, and the optical density in the wavelength ranges 400 nm-430 nm and 650 nm-670 nm is 4 or greater (FIG. 26L). Therefore, the excitation lights in the narrow-band wavelength regions A and B are sufficiently shielded by the excitation light cut-off filter 62.

If the endoscope operator presses a switch arranged on the operating panel of the light source unit 3, an instruction is given to commence acquisition of a fluorescent image using the fluorescent endoscope device, and the light source unit 3 is switched to the excitation light generating mode. At the same time, signals are sent to synchronize the timing of reading out image signals from the imaging unit 1, or the timing of changing the air gap spacing of the etalon 63, with the timing of shielding the excitation lights. Optical filters (e), (e) and an optical filter (f) that are used for fluorescent light image observation are arranged on the rotating disc 24, and are repetitively inserted into the light flux of the light source unit 3. Each of the optical filters (e), (e) has a % transmittance of 50% or greater in the wavelength range of 400 nm-430 nm, and the optical filter (f) has a % transmittance of 50% or greater in the wavelength range of 650 nm-670 nm. The illumination unit repetitively interposes shielding periods between the excitation light illumination periods, and the three illumination periods A1, A2 and B1 are repeated with each revolution of the rotating disc 24.

Figure 26B:
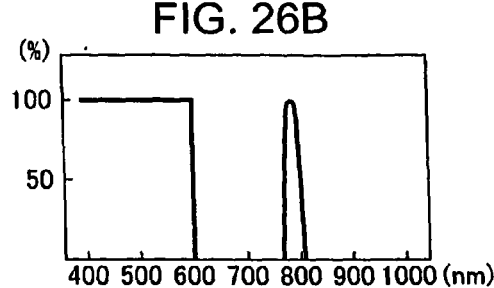
Figure 26G:
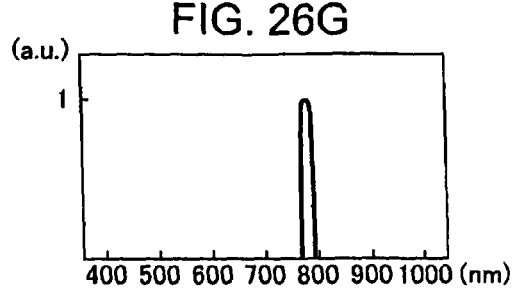
Figure 26C:
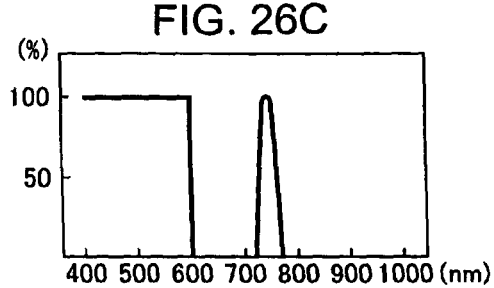
Figure 26H:
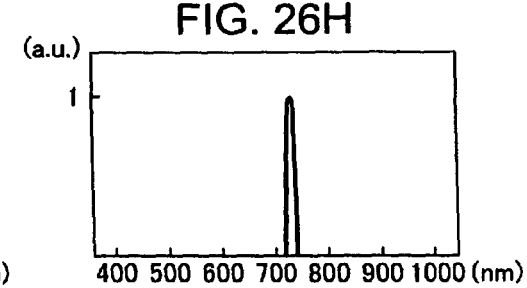
Figure 26D:
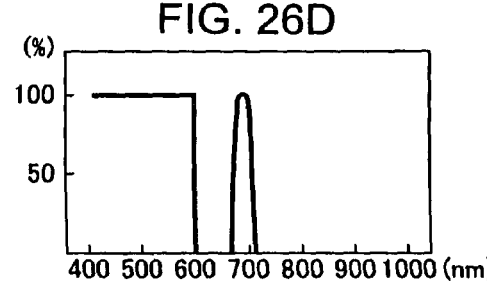
Figure 26I:
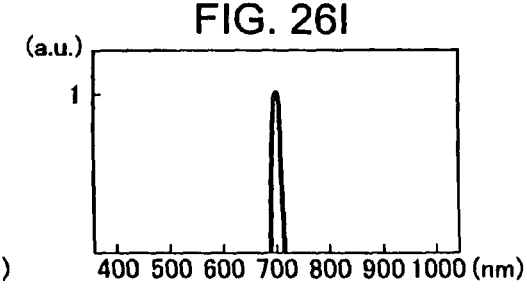
Figure 26E:
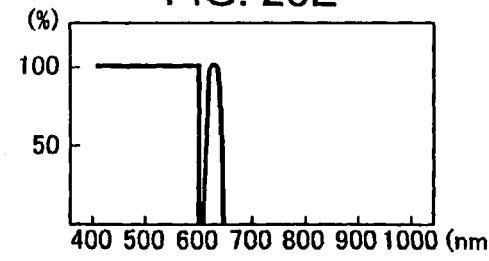

The etalon 63 has its air gap spacing changed by control signals from a drive circuit 4b, and it may be set to any one of at least five states having different transmission characteristics. In the periods during which the light source unit 3 creates the excitation light in the narrow-band wavelength region A, the etalon 63 is sequentially set to the following two states:

state 1—a state wherein, of the fluorescent light generated in the wavelength regions a1-a5, only light in the wavelength region a1 is substantially transmitted (FIG. 26F); and state 2—a state wherein, of the fluorescent light generated in the wavelength regions a1-a5, only light in the wavelength regions a1 and a2 is substantially transmitted (FIG. 26E).

In state 1, the air gap spacing of the etalon 63 is set to be the longest of the five states. At this time, the second wavelength transmission region of the etalon 63 is such that there is a peak transmittance at a wavelength that is longer than 800 nm, and the full width of the intensity profile as measured between the half-maximum intensity points is 30 nm or less.

In state 2, the air gap spacing of the etalon 63 is set to be the shortest of the five states. At this time, the second wavelength transmission region of the etalon is such that there is a peak transmittance in the wavelength range of 610 nm-640 nm, and the full width of the intensity profile as measured between the half-maximum intensity points is 30 nm or less.

Figure 26J:
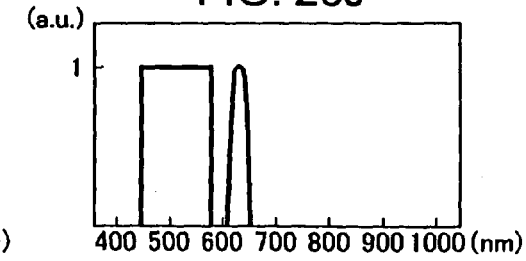
Figure 26F:
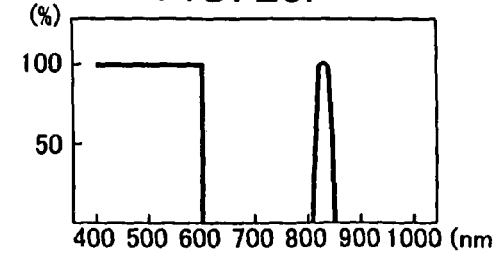
Figure 26K:
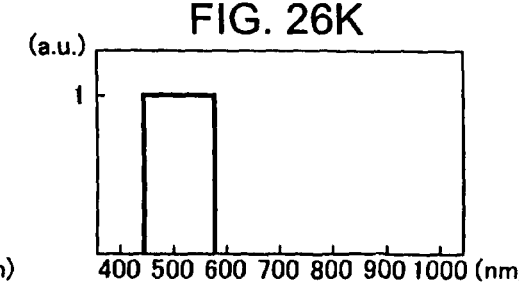

When the etalon 63 is set to state 1, of the fluorescent lights in the wavelength regions a1-a5, the image pickup device 64 receives only the fluorescent light in the wavelength region a1 (FIG. 26K). When the etalon 63 is set to state 2, of the fluorescent lights in the wavelength regions a1-a5, the image pickup device 64 receives only fluorescent light in the wavelength regions a1 and a2 (FIG. 26J).

One the other hand, in the period in which the light source unit 3 is creating excitation light in the narrow-band wavelength region B, the etalon 63 is set to the following three states:

state 3—a state wherein, of the fluorescent light generated in the wavelength regions a1-a5, only light in the wavelength regions a1 and a3 is substantially transmitted (FIG. 26D);

state 4—a state wherein, of the fluorescent light generated in the wavelength regions a1-a5, only light in the wavelength regions a1 and a4 is substantially transmitted (FIG. 26C); and state 5—a state wherein, of the fluorescent light generated in the wavelength regions a1-a5, only light in the wavelength regions a1 and a5 is substantially transmitted (FIG. 26B).

In states 3-5, the air gap spacings of the etalon 63 are greater than the air gap spacing in state 2 and smaller than the air gap spacing in state 1. In addition, the air gap spacing in state 3 is smaller than the air gap spacing in state 4, and the air gap spacing in state 4 is smaller than the air gap spacing in state 5.

When the etalon 63 is set to state 3, the second wavelength transmission range of the etalon 63 is such that there is a peak transmittance in the wavelength range of 690 nm-710 nm, and the full width of the intensity profile as measured between the half-maximum intensity points is 30 nm or less. At this time, fluorescent light in the wavelength region a3 is received by the image pickup device 64 (FIG. 26I).

When the etalon 63 is set to state 4, the second wavelength transmission region of the etalon 63 is such that there is a transmission peak in the wavelength range of 720 nm-740 nm, and the full width of the intensity profile as measured between the half-maximum intensity points is 30 nm or less. At this time, the fluorescent light in the wavelength region a4 is received by the image pickup device 64 (FIG. 26H).

When the etalon 63 is set to state 5, the second wavelength transmission region of the etalon is such that there is a transmission peak in the wavelength range of 770 nm-790 nm, and the full width of the intensity profile as measured between the half-maximum intensity points is 30 nm or less. At this time, fluorescent light in the wavelength region a5 is received by the image pickup device 64 (FIG. 26G).

Figure 27:
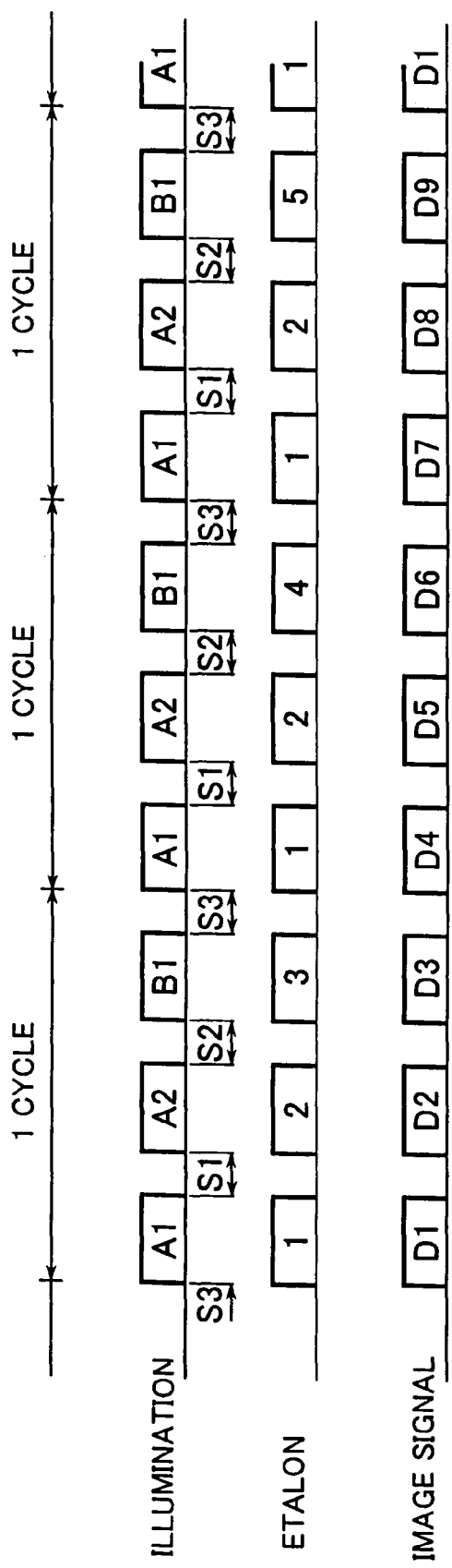
FIG. 27 is a timing chart showing the timing relationships during operation of the fluorescent endoscope device of Embodiment 3 for three cycles of the rotating disc 24, including the illumination periods, the etalon states, and the image signals acquired by the imaging unit.

FIG. 27 is a timing chart showing the timing among the illumination periods, the states of the etalon, and fluorescent image signals obtained by the image pickup device of Embodiment 3 over three cycles of illumination using the rotary disc 24. As shown in FIG. 27, if a cycle is taken as from the commencement of a first illumination period A1 (in which the illumination unit 2 irradiates light in the narrow-band wavelength region A) to the end of the third illumination period B1 (in which the illumination unit 2 irradiates excitation light in the narrow-band wavelength region B), image data necessary for image processing for the fluorescent endoscope device of this embodiment must be obtained over three consecutive cycles.

During a first illumination period A1 of the first cycle, the illumination unit 2 irradiates excitation light in the narrow-band wavelength region A. With the etalon 63 set so as to be in state 1, the imaging unit 1 acquires image signals D1 of fluorescent light in the wavelength region a1. The image signals D1 are then read out during the next period S1 in which the excitation light is shielded and are stored in the memory circuit 5a of the image processing unit 5.

During a second illumination period A2 of the first cycle, the illumination unit 2 illuminates excitation light in the narrow-band wavelength region A and the etalon 63 is set to state 2. As a result, the imaging unit 1 acquires the image signals D2 of fluorescent light in the wavelength regions a1 and a2. The image signals D2 are then read out during the next period S2 in which the excitation light is shielded and are stored in the memory circuit 5a of the image processing unit 5.

During a third illumination period B1 of the first cycle, the illumination unit 2 illuminates excitation light in the narrow-band wavelength region B and the etalon 63 is set to state 3. As a result, the imaging unit 1 acquires the image signals D3 of fluorescent light in the wavelength region a3. The image signals D3 are read out during the next period S3 in which the excitation light is shielded and are stored in the memory circuit 5a of the image processing unit 5.

During a first illumination period A1 of the second cycle, the illumination unit 2 irradiates excitation light in the narrow-band wavelength region A. With the etalon 63 set so as to be in state 1, the imaging unit 1 acquires image signals D4 of fluorescent light in the wavelength region a1. The image signals D4 are then read out during the next period S1 in which the excitation light is shielded and are stored in the memory circuit 5a of the image processing unit 5.

During a second illumination period A2 of the second cycle, the illumination unit 2 illuminates excitation light in the narrow-band wavelength region A and the etalon 63 is set to state 2. As a result, the imaging unit 1 acquires the image signals D5 of fluorescent light in the wavelength regions a1 and a2. The image signals D5 are then read out during the next period S2 in which the excitation light is shielded and are stored in the memory circuit 5a of the image processing unit 5.

During a third illumination period B1 of the second cycle, the illumination unit 2 illuminates excitation light in the narrow-band wavelength region B and the etalon 63 is set to state 4. As a result, the imaging unit 1 acquires the image signals D6 of fluorescent light in the wavelength region a4. The image signals D6 are then read out during the next period S3 in which the excitation light is shielded and are stored in the memory circuit 5a of the image processing unit 5.

During a first illumination period A1 of the third cycle, the illumination unit 2 irradiates excitation light in the narrow-band wavelength region A. With the etalon 63 set so as to be in state 1, the imaging unit 1 acquires image signals D7 of fluorescent light in the wavelength region a1. The image signals D7 are then read out during the next period S1 in which the excitation light is shielded and are stored in the memory circuit 5a of the image processing unit 5.

During a second illumination period A2 of the third cycle, the illumination unit 2 illuminates excitation light in the narrow-band wavelength region A and the etalon 63 is set to state 2. As a result, the imaging unit 1 acquires the image signals D8 of fluorescent light in the wavelength regions a1 and a2. The image signals D8 are then read out during the next period S2 in which the excitation light is shielded and are stored in the memory circuit 5a of the image processing unit 5.

During a third illumination period B1 of the third cycle, the illumination unit 2 illuminates excitation light in the narrow-band wavelength region B and the etalon 63 is set to state 5. As a result, the imaging unit 1 acquires the image signals D9 of fluorescent light in the wavelength region a5. The image signals D9 are then read out during the next period S3 in which the excitation light is shielded and are stored in the memory circuit 5a of the image processing unit 5.

Image processing is accomplished based on the image signals acquired during the above-discussed three cycles. The procedure of image processing of the read-out image signals that is accomplished by the image processing unit 5 of this embodiment is the same as that described previously, and therefore further explanation will be omitted.

Figure 28A:
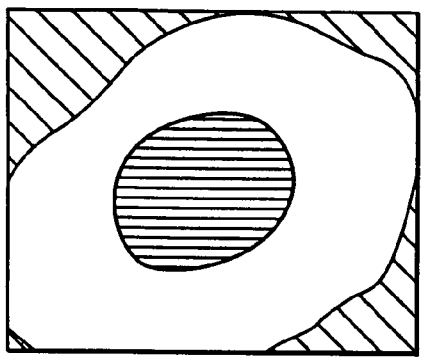
FIGS. 28A-28D are various diagrams showing typical types of fluorescent images that may be displayed on a TV monitor 7 using a fluorescent endoscope device according to Embodiment 3.
Figure 28B:
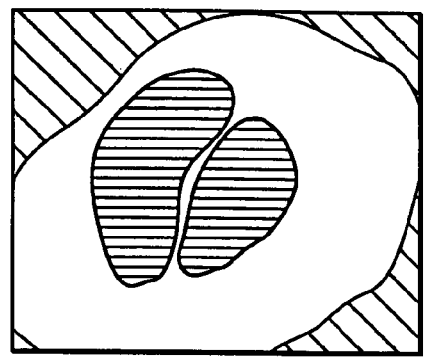
Figure 28C:
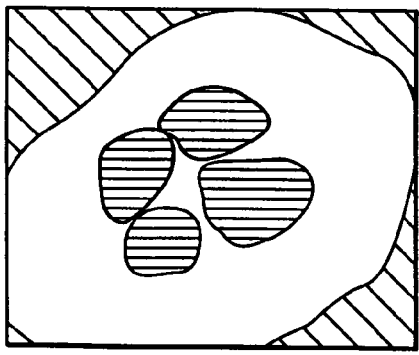
Figure 28D:
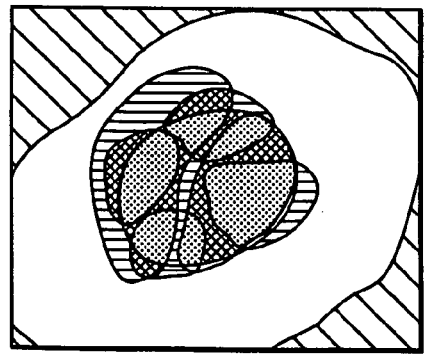

FIGS. 28A-28D are schematic diagrams that illustrate the kinds of fluorescent images that can be displayed on a TV monitor using the fluorescent endoscope device of Embodiment 3. FIG. 28A is a quasi-color-coded image that may be prepared based on the three kinds of image signals that are read out during the first cycle. With a quasi-color-coded image, a normal part, a part in which the surface layer of normal tissue is inflamed, and a pathologically changing part can the displayed in separate colors. FIG. 28B is a quasi-color-coded image that may be prepared based on three types of image signals that are read out during the second cycle. FIG. 28C is a quasi-color-coded image that may be prepared based on three types of image signals that are read out during the third cycle. FIG. 28D is a composite quasi-color-coded image that may be prepared based on the images shown in FIGS. 28A-28C. In the case where the pathologically changing parts in FIGS. 28A-28C overlap, the overlapping portions may be emphatically displayed as a contour drawing. The image shown in FIG. 28A includes information relating to a substance k1 that originates in pathologically changing tissue. The image shown in FIG. 28B includes information relating to a different substance k2 that originates in pathologically changing tissue. The image shown in FIG. 28C includes information relating to a yet another substance k3 that originates in pathologically changing tissue. Therefore, a composite image as shown in FIG. 28D can be prepared, utilizing the information contained in FIGS. 28A-28C, that enables an observer to more easily see the lesion tissue areas and thus such an image provides a higher degree of reliability in terms of identifying lesion tissue.

In the present embodiment as well, in lieu of using an etalon 63, an array of five types (i.e., each of a different peak transmittance) of optical filters can be arranged so that the optical filters overlay different pixel elements of an image pickup device. If multiple fluorescent images having different peak wavelengths are imaged by the imaging unit 1, the array of five types of optical filters having different peak transmittances enables the multiple fluorescent images to be individually detected.

For example, the following five types of optical filters may be used:

(1) an optical filter wherein the % transmittance is 50% or greater in the wavelength range of 420 nm-580 nm, and the average % transmittance is 5% or less for other wavelengths in the range of 400 nm-800 nm;

(2) an optical filter wherein the % transmittance is 50% or greater in the wavelength range of 610 nm-640 nm, and the average % transmittance is 5% or less for other wavelengths in the range of 400 nm-800 nm;

(3) an optical filter wherein the % transmittance is 50% or greater in the wavelength range of 690 nm-710 nm, and the average % transmittance is 5% or less for other wavelengths in the range of 400 nm-800 nm;

(4) an optical filter wherein the % transmittance is 50% or greater in the wavelength range of 720 nm-740 nm, and the average % transmittance is 5% or less for other wavelengths in the range of 400 nm-800 nm; and (5) an optical filter wherein the % transmittance is 50% or greater in the wavelength range of 770 nm-790 nm, and the average % transmittance is 5% or less for other wavelengths in the range of 400 nm-800 nm.

By, for example, arranging the optical filters that have the same transmission characteristics in columns so that different optical filters overlay different pixels in a row, if a fluorescent image is imaged for each row of optical filters, then multiple fluorescent images can be individually acquired. With such a composition, it is possible to successively read out image signals, and there is no need to provide light shielding periods in order to read out image signals. Therefore, bright images can be acquired even from a relatively weak fluorescent substance. In addition, since the fluorescent light having different peak wavelengths can be separated, the excitation light in the narrow-band wavelength region A and the excitation light in the narrow-band wavelength region B can be simultaneously irradiated, making it possible to simplify the structure of the light source unit. In addition, since multiple fluorescent images can be individually acquired, computation processing can be eliminated from the image processing unit 5.

In the embodiments discussed above, which are provided with a light source unit for generating excitation lights having different peak wavelengths, an illumination unit for irradiating the excitation light onto a living tissue and an imaging unit including a variable optical element for changing the transmission wavelength thereof, it is desirable that the following Condition (1) be satisfied:

$$n<m<3n \qquad \text{Condition (1)}$$

where n is the number of excitation lights of the light source unit having different peak wavelengths and is an integer greater than 1; and m is the number of fluorescent images of different peak wavelengths that are acquired by the imaging unit.

If the lower limit of Condition (1) is not satisfied, it becomes difficult to diagnose a pathological tissue that has little histological change such as early stages of cancer with high accuracy since the information regarding a pathologically changing part that may be obtained from the acquired images is insufficient. On the other hand, if the upper limit of Condition (1) is not satisfied, the excitation lights of the light source unit will be unable to provide adequate excitation energy for all of the fluorescent probes, resulting in being unable to obtain images with sufficient brightness from each type of optical probe used.

In addition, in the embodiments discussed above, which are provided with a light source unit for generating excitation lights having different peak wavelengths, an illumination unit for irradiating the excitation light onto a living tissue, and an imaging unit including an image pickup device and multiple optical filters that have different transmission wavelength bands and are arranged on each pixels of the image pickup device, it is desirable that the following Condition (2) be satisfied:

$$n<k<3n \qquad \text{Condition (2)}$$

where n is the number of excitation lights of the light source unit having different peak wavelengths and is an integer greater than 1; and k is the number of types of optical filters that have different peak transmittance wavelengths.

If the lower limit of Condition (2) is not satisfied, it becomes difficult to diagnose a pathological tissue that has little histological change, such as often occurs in early stages of cancer, with high accuracy since the information regarding a pathologically changing part obtained from the acquired images is insufficient. On the other hand, if the upper limit of Condition (2) is not satisfied, light source unit 3 will be unable to provide adequate excitation energy for all of the fluorescent probes; this will result in being unable to obtain images with sufficient brightness from each type of optical probe used. Also, the number of types of the optical filters for distinguishing different fluorescent lights will be large. This results in reducing the number of pixels allocated for each type of filter. Therefore, there will not be sufficient resolution to accomplish imaging for each type of optical filter.

The fluorescent endoscope device according to the present invention may be used in detecting and diagnosing pathological changes in living organisms and, more particularly, pathological changes that occur in the early stages of various cancers.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An endoscope device comprising:

a light source unit that creates multiple excitation lights having different peak wavelengths said multiple excitation lights include a first excitation light having wavelength components that excite one or more naturally occurring substances within a living organism, and a second excitation light having wavelength components that excite two or more fluorescent substances that have been administered to a living organism;

an illumination unit that optically transmits the multiple excitation lights to a distal end of the endoscope device, and the multiple excitation lights are then directed so as to illuminate a living organism; and an imaging unit that includes an objective optical system, a variable transmittance optical element, and an image pickup device;

wherein the variable transmittance optical element has a transmittance of 50% or greater for wavelengths less than 600 nm, and for wavelengths 600 nm or greater, the wavelength transmission range may be varied so that said two or more fluorescent substances that have been administered to a living organism may be separately detected;

the imaging unit is capable of acquiring images of fluorescent light having different peak wavelengths, and the following condition is satisfied:

$n < m < 3n$ where
n is the number of excitation lights having different peak wavelengths created by the light source unit and an integer greater than 1; and
m is the number of fluorescent images having different peak wavelengths that are acquired by the imaging unit.

2. The endoscope device according to claim 1,
wherein the multiple excitation lights include:
a first excitation light having wavelengths of less than 500 nm that excite an auto-fluorescent substance that occurs naturally within a living organism; and
a second excitation light having wavelengths of 500 nm or more that excite fluorescent substances administered to the living organism from outside of the living organism.

3. The endoscope device according to claim 2, wherein:
the first excitation light has wavelength components in a narrow-band wavelength region that includes 405 nm;
the second excitation light has wavelength components in a narrow-band wavelength region that includes 660 nm; and
the full widths of the intensity profiles of said excitation lights in the narrow-band wavelength regions, as measured between the half-maximum intensity points, are 30 nm or less.

4. The endoscope device according to claim 2, wherein:
the light source unit is capable of being switched from a first illumination state that creates narrow-band excitation light having wavelengths in the range of 400 nm-430 nm to a second illumination state that creates narrow-band excitation light having wavelengths that are within the wavelength range of 650 nm-700 nm, and vice-versa; and
an optical filter is arranged in the imaging unit that cuts off the excitation lights that are created in the first illumination state and in the second illumination state.

5. The endoscope device according to claim 4, wherein:
the light source unit includes multiple semiconductor elements that each create coherent light having different peak wavelengths.

6. The endoscope device according to claim 4, wherein:
the endoscope device further includes an image processing unit that generates an image from image signals that have been acquired by the image pickup device; and
the image processing unit, at a minimum, generates multiple images having different peak wavelength components based on image signals acquired by the image pickup device during the illumination period of the first illumination state.

7. The endoscope device according to claim 4, wherein:
the endoscope device further includes an image processing unit that forms images from signals acquired by the image pickup device; and
the image processing unit is composed so that, in addition to forming multiple images from image signals acquired by the image pickup device in the periods in which the excitation lights are illuminated, it is also capable of forming a composite image from among these image signals.

8. The endoscope device according to claim 5, wherein:
the multiple semiconductor elements create coherent lights in which 405 nm is a peak wavelength and in which 660 nm is a peak wavelength.

9. The endoscope device according to claim 5, and further including:
a control unit that controls the operation of the light source unit and the imaging unit;
wherein
the control unit includes a timing control circuit that controls the light exposure time of the image pickup device, and the lighting and extinguishing of each of the multiple semiconductor elements is controlled at different timing with each other by the timing control circuit.

10. The endoscope device according to claim 5, wherein:
the illumination unit includes a light guide for optically transmitting excitation light created by the multiple semiconductor elements to the distal end of the endoscope; and
the light source unit includes a light chopper that may be inserted into, or removed from,
the light paths between the multiple semiconductor elements and an end surface of the light guide, and the light chopper shields coherent light created by one of the semiconductor elements and coherent light created by the other of the semiconductor elements at different timings.

11. The endoscope device according to claim 5, wherein:
the illumination unit is provided with a light guide as a means for optically transmitting excitation light created by the multiple semiconductor elements to the distal end of the endoscope device; and
the light source unit includes a chopper that may be inserted into/removable from the light path between the multiple semiconductor elements and the end surface of the light guide such that the chopper shields, at different timings, the coherent light created by the multiple semiconductor elements.

12. An endoscope device comprising:
a light source unit that creates multiple excitation lights having different peak wavelengths;
an illumination unit that optically transmits the excitation lights to a distal end of the endoscope device so as to then be directed to illuminate a living organism; and
an imaging unit which includes an objective optical system, an image pickup device and multiple types of optical filters, each type of which has different peak transmittance wavelength, arranged in front of an image receiving surface of the image pickup device, and which acquires multiple fluorescent images of the living organism so that two or more fluorescent substances, that emit fluorescence at different peak wavelengths and that have been administered to a living organism, may be separately detected;
wherein
the light source unit creates at least two excitation lights having different peak wavelengths, namely, a first excitation light having wavelength components that excite one or more naturally occurring substances within a living organism, and a second excitation light having wavelength components that excite said two or more fluorescent substances that have been administered to the living organism;
the first excitation light has wavelength components in a narrow-band wavelength region that includes 405 nm;
the second excitation light has wavelength components in a narrow-band wavelength region that includes 660 nm;
the full widths of the intensity profiles of said excitation lights in the narrow-band wavelength regions, as measured between the half-maximum intensity points, are 30 nm or less; and the following condition is satisfied:

n<k<3n where
n is the number of excitation lights having different peak transmittance wavelengths that are created by the light source unit and is an integer greater than 1; and
k is the number of different types of optical filters having different peak transmittance wavelengths.

13. The endoscope device according to claim 12, wherein the different types of optical filters are arranged so as to overlay different pixels of the image pickup device in a manner so that multiple fluorescent images having different peak wavelengths can be individually acquired by the imaging unit via the respective different types of optical filters.

14. The endoscope device according to claim 12, wherein the different types of optical filters include the following three optical filters having different spectral transmittance characteristics, as follows:
(1) an optical filter in which the average % transmittance is 50% or greater for the wavelength range of 420 nm-580 nm, and the average % transmittance is 5% or less for other wavelengths in the wavelength range of 400 nm-800 nm;
(2) an optical filter in which the average % transmittance is 50% or greater for the wavelength range of 610 nm-640 nm, and the average % transmittance is 5% or less for other wavelengths in the wavelength range of 400 nm-800 nm; and
(3) an optical filter in which the average % transmittance is 50% or greater for the wavelength range of 710 nm-740 nm, and the average % transmittance is 5% or less for other wavelengths in the wavelength range of 400 nm-800 nm.

15. The endoscope device according to the claim 12, wherein the different types of optical filters include the following four optical filters having different spectral transmittance characteristics, as follows:
(1) an optical filter in which the average % transmittance is 50% or greater for the wavelength range of 420 nm-580 nm, and the average % transmittance is 5% or less for other wavelengths in the wavelength range of 400 nm-800 nm;
(2) an optical filter in which the average % transmittance is 50% or greater for the wavelength range of 610 nm-640 nm, and the average % transmittance is 5% or less for other wavelengths in the wavelength range of 400 nm-800 nm;
(3) an optical filter in which the average % transmittance is 50% or greater for the wavelength range of 710 nm-740 nm, and the average % transmittance is 5% or less for other wavelengths in the wavelength range of 400 nm-800 nm; and
(4) an optical filter in which the average % transmittance is 50% or greater for the wavelength range of 770 nm-800 nm, and the average % transmittance is 5% or less for other wavelengths in the wavelength range of 400 nm-800 nm.

16. The endoscope device according to the claim 12, wherein the different types of optical filters include the following five optical filters having different spectral transmittance characteristics as follows:
(1) an optical filter in which the average % transmittance for the wavelength range of 420 nm-580 nm is 50% or greater, and the average % transmittance for other wavelengths in the range of 400 nm-800 nm is 5% or less;
(2) an optical filter in which the average % transmittance for the wavelength range of 610 nm-640 nm is 50% or greater, and the average % transmittance for other wavelengths in the range of 400 nm-800 nm is 5% or less;
(3) an optical filter in which the average % transmittance for the wavelength range of 690 nm-710 nm is 50% or greater, and the average % transmittance for other wavelengths in the range of 400 nm-800 nm is 5% or less;
(4) an optical filter in which the average % transmittance for the wavelength range of 720 nm-740 nm is 50% or greater, and the average % transmittance for other wavelengths in the range of 400 nm-800 nm is 5% or less; and
(5) an optical filter in which the average % transmittance for the wavelength range of 770 nm-790 nm is 50% or greater, and the average % transmittance for other wavelengths in the range of 400 nm-800 nm is 5% or less.

17. An imaging unit of an endoscope that includes a variable transmittance optical element that enables the wavelength of peak transmittance to be varied by changing an air gap spacing of the variable transmittance optical element, wherein:
in a first wavelength transmission range for wavelengths less than 600 nm, the average % transmittance of the variable transmittance optical element is maintained at 50% or greater even when the air gap spacing is changed so as to allow naturally ocurring fluoresence in a living organism to be detected and, in a second wavelength transmission range of 600 nm or greater, the wavelength region transmitted by the variable transmittance optical element changes as the air gap spacing is changed to thereby enable fluorescence from two or more fluorescent substances that have been administered to a living organism and which have different wavelength regions in which they emit fluorescence, to be separately detected by the imaging unit.

18. The imaging unit of claim 17, wherein the variable transmittance optical element is capable of switching among at least the following three states:
state 2—a state having a peak transmittance in the range of 610 nm-640 nm;
state 3—a state having a peak transmittance in the range of 710 nm-740 nm; and
state 1—a state having no peak transmittance in the range of 600 nm-740 nm.

19. The imaging unit of claim 17, wherein the variable transmittance optical element is capable of switching to each state among the following four states:
state 2—a state having a peak transmittance in the range of 610 nm-640 nm;
state 3—a state having a peak transmittance in the range of 710 nm-740 nm;
state 4—a state having a peak transmittance in the range of 770 nm-800 nm; and
state 1—a state having no peak transmittance in the range of 600 nm-800 nm.

20. The imaging unit according to claim 17, wherein the variable transmittance optical element is capable of switching among the five following states:
state 2—a state having a peak transmittance in the range of 610 nm-640 nm;
state 3—a state having a peak transmittance in the range of 690 nm-710 nm;
state 4—a state having a peak transmittance in the range of 720 nm-740 nm;
state 5—a state having a peak transmittance in the range of 770 nm-790 nm; and state 1—a state having no peak transmittance in the range of 600 nm-800 nm.

21. An endoscope device comprising:
a light source unit that creates multiple excitation lights of different peak wavelengths so as to excite fluorescent substances that occur naturally in living organisms as well so as to excite two or more fluorescent probes that have been administered to the living organism, said two or more fluorescent probes having different wavelength ranges in which they emit fluorescence;
an illumination unit that illuminates the multiple excitation lights onto a living organism;
an imaging unit that images fluorescent light received from the living organism; and
an image processing unit that constructs images using image signals acquired by the imaging unit;
wherein
the imaging unit includes an etalon having an air gap spacing that may be changed so that, in a first wavelength transmission range of less than 600 nm, the average % transmittance of the etalon is maintained at 50% or more even when the air gap spacing is changed, and in a second wavelength transmission range of 600 nm or greater, the wavelength region transmitted changes as the air gap spacing of the etalon is changed so as to allow the fluorescence from said two or more fluorescent probes to be separately detected, and the etalon is capable of being switched between at least the following two states:
state 2—a state having a peak transmittance in the range of 610 nm-640 nm, and
state 3—a state having a peak transmittance in the range of 710 nm-740 nm.

22. The endoscope device of claim 21, wherein:
the light source unit may be switched between a first illumination state that creates excitation light having wavelengths within the wavelength range of 400 nm-430 nm, and a second illumination state that creates excitation light having wavelengths in the range 650 nm-670 nm; and
the imaging unit includes an excitation light cut-off filter that attenuates the excitation light created in the first illumination state and in the second illumination state.

23. The endoscope device of claim 22, wherein the sum of the optical density of the excitation light cut-off filter and the optical density of the etalon, throughout the wavelength ranges of 400-430 nm and 650 nm-670 nm, is greater than or equal to 4.

24. The endoscope device of claim 21, wherein the image processing unit includes an operating circuit that uses data obtained from multiple image signals that are obtained during different etalon states.

25. The endoscope device of claim 24, wherein the operating circuit subtracts the intensity of image signals acquired by the imaging unit when the etalon is in a state other than the first state from the intensity of image signals acquired by the imaging unit when the etalon is in the first state.

26. An endoscope device comprising:
a light source unit that creates multiple excitation lights having different peak wavelengths;
an illumination unit that illuminates the multiple excitation lights onto a living organism;
an imaging unit that forms and acquires fluorescent images of the living organism; and
an image processing unit which constructs images by processing image signals acquired by the imaging unit;
wherein
the imaging unit includes an etalon having an air gap spacing that may be changed so as to provide a first wavelength transmission range in which, even if the air gap spacing is changed, the average % transmittance is maintained at 50% or greater for incident wavelengths shorter than 600 nm, and a second wavelength transmission range in which, for incident wavelengths of 600 nm or longer, the peak transmittance wavelength changes when the air gap spacing changes so as to allow the fluorescence from two or more fluorescent probes that have been administered to the living organism to be separately detected, and the etalon is capable of switching between the following three states:
state 2—a state having a peak transmittance in the range of 610 nm-640 nm;
state 3—a state having a peak transmittance in the range of 710 nm-740 nm; and
state 4—a state having a peak transmittance in the range of 770 nm-800 nm.

27. The endoscope device according to claim 26, wherein:
the light source unit is capable of switching between a first illumination state which creates excitation light in the wavelength range of 400 nm-430 nm, and a second illumination state which creates excitation light in the wavelength range of 680 nm-700 nm; and,
an excitation light cut-off filter, that attenuates the excitation lights created in the first illumination state and in the second illumination state, is arranged in the imaging unit.

28. The endoscope device of claim 27, wherein the sum of the optical density of the excitation light cut-off filter and the optical density of the etalon, throughout the wavelength ranges of 400 nm-430 nm and 680 nm-700 nm, is greater than or equal to 4.

29. The endoscope device of claim 26, wherein the image processing unit is provided with an operating circuit that uses data from multiple image signals that are acquired while the imaging unit is in different etalon states.

30. The endoscope device of claim 29, wherein the operating circuit subtracts the intensity of image signals acquired by the imaging unit when the etalon is in a state other than the first state from the intensity of image signals acquired by the imaging unit when the etalon is in the first state.

31. An endoscope device comprising:
a light source unit that creates multiple excitation lights having different peak wavelengths;
an illumination unit that illuminates the multiple excitation lights onto a living organism;
an imaging unit that images and detects fluorescent light from the living organism; and
an image processing unit that forms images by processing image signals acquired by the imaging unit; wherein
the imaging unit has a first wavelength transmission range in which, even if the air gap spacing is changed, the average % transmittance is maintained at 50% or greater for incident wavelengths less than 600 nm, and a second wavelength transmission range in which, for incident wavelengths of 600 nm or longer, the peak transmittance wavelength changes when the air gap spacing changes so as to allow the fluorescence from three fluorescent probes that have been administered to the living organism to be separately detected in different wavelength regions, and the etalon is capable of switching among the following four states:
state 2—a state having a peak transmittance in the range of 610 nm-640 nm;

state 3—a state having a peak transmittance in the range of 690 nm-710 nm;
state 4—a state having a peak transmittance in the range of 720 nm-740 nm; and
state 5—a state having a peak transmittance in the range of 770 nm-790 nm.

32. The endoscope device according to claim 31, wherein:
the light source unit is capable of switching between a first illumination state that creates excitation light within a wavelength range of 400 nm-430 nm, and a second illumination state that creates excitation light within a wavelength range of 650 nm-670 nm; and
an excitation light cut-off filter is arranged in the imaging unit that attenuates the excitation lights created in the first illumination state and in the second illumination state.

33. The endoscope device of claim 32, wherein:
the sum of the optical density of the excitation light cut-off filter and the optical density of the etalon, throughout the wavelength ranges of 400 nm-430 nm and 650 nm-670 nm is greater than or equal to 4.

34. The endoscope device of claim 3, and wherein the image processing unit includes an operating circuit that uses data from multiple image signals that are acquired while the etalon state of the imaging unit is being switched.

35. The endoscope device of claim 34, wherein the operating circuit subtracts the intensity of image signals that are acquired by the imaging unit when the etalon is in a state other than the first state from the intensity of image signals acquired by the imaging unit when the etalon is in the first state.

* * * * *